United States Patent
Tonnel et al.

(10) Patent No.: US 9,828,359 B2
(45) Date of Patent: Nov. 28, 2017

(54) PROCESS FOR THE PREPARATION OF 3-SUBSTITUTED (INDOL-1-YL)-ACETIC ACID ESTERS

(71) Applicant: Atopix Therapeutics Limited, London (GB)

(72) Inventors: Jacques Tonnel, Elne (FR); Sylvie Blanchet, Feneu (FR); Guillaume Léonard Pierre Dewaele, Saint Georges sur Loire (FR)

(73) Assignee: Atopix Therapeutics Limited, London (GB)

( * ) Notice: Subject to any disclaimer, the term of this patent is extended or adjusted under 35 U.S.C. 154(b) by 0 days.

(21) Appl. No.: 15/307,998

(22) PCT Filed: Dec. 12, 2014

(86) PCT No.: PCT/GB2014/053686
§ 371 (c)(1),
(2) Date: Oct. 31, 2016

(87) PCT Pub. No.: WO2015/092372
PCT Pub. Date: Jun. 25, 2015

(65) Prior Publication Data
US 2017/0305879 A1    Oct. 26, 2017

(30) Foreign Application Priority Data
Dec. 17, 2013  (GB) .................................. 1322273.2

(51) Int. Cl.
C07D 401/06    (2006.01)

(52) U.S. Cl.
CPC ................................. C07D 401/06 (2013.01)

(58) Field of Classification Search
CPC .................................................. C07D 401/06
See application file for complete search history.

(56) References Cited

U.S. PATENT DOCUMENTS

| | | | |
|---|---|---|---|
| 3,489,767 A | 1/1970 | Yamamoto et al. | |
| 3,557,142 A | 1/1971 | Bell | |
| 4,273,782 A | 6/1981 | Cross et al. | |
| 4,363,912 A | 12/1982 | Cross et al. | |
| 4,859,692 A | 8/1989 | Bernstein et al. | |
| 4,966,911 A | 10/1990 | Clark et al. | |
| 5,330,997 A | 7/1994 | Mylari et al. | |
| 6,214,991 B1 | 4/2001 | Jones et al. | |
| 6,426,344 B2 | 7/2002 | Jones et al. | |
| 6,521,659 B2 | 2/2003 | Sredy et al. | |
| 6,730,794 B2 | 5/2004 | Jones et al. | |
| 6,964,980 B2 | 11/2005 | Sredy et al. | |
| 7,105,514 B2 | 9/2006 | Jones et al. | |
| 7,348,351 B2 | 3/2008 | Jennings et al. | |
| 7,582,672 B2 | 9/2009 | Middlemiss et al. | |
| 7,750,027 B2 | 7/2010 | Armer et al. | |
| 7,919,512 B2 | 4/2011 | Armer et al. | |
| 7,999,119 B2 | 8/2011 | Armer et al. | |
| 8,044,088 B2 | 10/2011 | Armer et al. | |
| 8,163,931 B2 | 4/2012 | Middlemiss et al. | |
| 8,163,936 B2 | 4/2012 | Middlemiss et al. | |
| 8,168,673 B2 | 5/2012 | Armer et al. | |
| 8,198,314 B2 | 6/2012 | Middlemiss et al. | |
| 8,268,878 B2 | 9/2012 | Armer et al. | |
| 8,314,257 B2 | 11/2012 | Middlemiss et al. | |
| 8,536,158 B2 | 9/2013 | Armer et al. | |
| 8,563,536 B2 | 10/2013 | Armer et al. | |
| 8,703,956 B2 | 4/2014 | Betancourt et al. | |
| 8,980,918 B2 | 3/2015 | Betancourt et al. | |
| 8,980,927 B2 | 3/2015 | Armer et al. | |
| 9,102,658 B2 | 8/2015 | Tonnel et al. | |
| 2003/0153751 A1 | 8/2003 | Seehra et al. | |
| 2004/0116488 A1 | 6/2004 | Jennings et al. | |
| 2005/0119268 A1 | 6/2005 | Middlemiss et al. | |
| 2007/0232681 A1 | 10/2007 | Middlemiss et al. | |
| 2009/0018138 A1 | 1/2009 | Middlemiss et al. | |
| 2009/0018338 A1 | 1/2009 | Middlemiss et al. | |
| 2009/0023788 A1 | 1/2009 | Middlemiss et al. | |
| 2009/0186923 A1 | 7/2009 | Armer et al. | |
| 2009/0192195 A1 | 7/2009 | Armer et al. | |
| 2010/0022613 A1 | 1/2010 | Armer et al. | |
| 2010/0035956 A1 | 2/2010 | Armer et al. | |
| 2010/0041699 A1 | 2/2010 | Boyd et al. | |

(Continued)

FOREIGN PATENT DOCUMENTS

| | | |
|---|---|---|
| EP | 0 054 417 B1 | 6/1982 |
| EP | 0 539 117 A1 | 4/1993 |

(Continued)

OTHER PUBLICATIONS

Cross, P.E., et al., "Selective Thromboxane Synthetase Inhibitors. 2. 3(1H-Imidazol-1-ylmethyl)-2-methyl-1H-indole-l-propanoic Acid and Analogues," *J. Med. Chem.* 29:342-346, American Chemical Society, United States (1986).

Emery, D.L., et al., "Prostaglandin $D_2$ causes accumulation of eosinophils in the lumen of the dog trachea," *J. Appl. Physiol.* 67(3):959-962, American Physiological Society, United States (1989).

Ettmayer, P., et al., "Lessons Learned from Marketed and Investigational Prodrugs," *Journal of Medicinal Chemistry* 47(10:2393-2404, American Chemical Society, United States (2004).

Fujitani, Y., et al., "Pronounced Eosinophilic Lung Inflammation and Th2 Cytokine Release in Human Lipocalin-Type Prostaglandin D Synthase Transgenic Mice," *The Journal of Immunology* 168:443-449, The American Association of Immunologists, Untied States (2002).

(Continued)

*Primary Examiner* — Timothy R Rozof
(74) *Attorney, Agent, or Firm* — Sterne, Kessler, Goldstein & Fox P.L.L.C.

(57) ABSTRACT

The invention relates to an industrial scale process for the preparation of a compound of general formula (I): (Formula (I)) wherein $R^1$, $R^2$ and $R^3$ are as defined herein. The process comprises reacting compounds of general formulae (II) and (III): (formulae (II), (III)) in the presence of a Lewis acid followed by a reduction with triethylsilane.

22 Claims, No Drawings

(56) References Cited

U.S. PATENT DOCUMENTS

| | | | |
|---|---|---|---|
| 2010/0056544 | A1 | 3/2010 | Lovell |
| 2010/0063103 | A1 | 3/2010 | Armer et al. |
| 2010/0266535 | A1 | 10/2010 | Armer et al. |
| 2010/0330077 | A1 | 12/2010 | Armer et al. |
| 2011/0123547 | A1 | 5/2011 | Armer et al. |
| 2011/0124683 | A1 | 5/2011 | Hunter et al. |
| 2011/0142855 | A1 | 6/2011 | Armer et al. |

FOREIGN PATENT DOCUMENTS

| | | |
|---|---|---|
| EP | 0 574 174 A2 | 12/1993 |
| EP | 1 170 594 A2 | 1/2002 |
| EP | 1 211 513 B1 | 6/2002 |
| EP | 0 851 030 B1 | 9/2005 |
| GB | 1 356 834 | 6/1974 |
| GB | 1 407 658 | 9/1975 |
| GB | 1 460 348 | 1/1977 |
| JP | 43-24418 | 4/1966 |
| JP | 2001-247570 A | 9/2001 |
| PL | 65781 | 10/1972 |
| WO | WO 93/12786 A1 | 7/1993 |
| WO | WO 95/06046 A1 | 3/1995 |
| WO | WO 9603376 A1 | 2/1996 |
| WO | WO 96/26207 A1 | 8/1996 |
| WO | WO 99/43651 A2 | 9/1999 |
| WO | WO 99/50268 A2 | 10/1999 |
| WO | WO 00/32180 A2 | 6/2000 |
| WO | WO 01/51489 A2 | 7/2001 |
| WO | WO 01/64205 A2 | 9/2001 |
| WO | WO 03/066046 A1 | 8/2003 |
| WO | WO 03/066047 A1 | 8/2003 |
| WO | WO 03/097042 A1 | 11/2003 |
| WO | WO 03/097598 A1 | 11/2003 |
| WO | WO 03/101961 A1 | 12/2003 |
| WO | WO 03/101981 A1 | 12/2003 |
| WO | WO 2004/058164 A2 | 7/2004 |
| WO | WO 2005/044260 A1 | 5/2005 |
| WO | WO 2006/095183 A1 | 9/2006 |
| WO | WO 2008/012511 A1 | 1/2008 |
| WO | WO 2009/090414 A1 | 7/2009 |
| WO | WO 2015/166274 A1 | 11/2015 |
| WO | WO 2015/166280 A1 | 11/2015 |

OTHER PUBLICATIONS

Gervais, F.G., et al., "Selective modulation of chemokinesis, degranulation, and apoptosis in eosinophils through the $PGD_2$ receptors CRTH2 and DP," *J Allergy Clin Immunol* 108:982-988, Mosby, Inc., United States (2001).

Hardy, C.C., et al., "The Bronchoconstrictor Effect of Inhaled Prostaglandin $D_2$ in Normal and Asthmatic Men," *The New England Journal of Medicine* 311(4):209-213, Massachusetts Medical Society, United States (1984).

Hirai, H., et al., "Prostaglandin D2 Selectively Induces Chemotaxis in T Helper Type 2 Cells, Eosinophils, and Basophils via Seven-Transmembrane Receptor CRTH2," *J. Exp. Med.* 193(2):255-261, The Rockefeller University Press, United States (2001).

International Search Report for International Application No. PCT/GB2014/053686, European Patent Office, Netherlands, dated Mar. 3, 2015, 3 pages.

Kumar, S., et al., "Novel indium-mediated ternary reactions between indole-3-carboxaldehydes-allyl bromide-enamines: facile synthesis of bisindolyl- and indoyl-heterocyclic alkanes," *Tetrahedron Letters* 44:2101-2104, Elsevier Science Ltd., England (2003).

Matassa, V.G. et al., "Evolution of a Series of Peptidoleukotriene Antagonists: Synthesis and Structure/Activity Relationships of 1,3,5-Substituted Indoles and Indalzoles," *J. Med. Chem.* 33:1781-1790, American Chemical Society, United States (1990).

Menciu, C., et al., "New N-(Pyridin-4-yl)-(indol-3-yl)acetamides and Propanamides as Antiallergic Agents," *J. Med. Chem..* 42:638-648, American Chemical Society, United States (1999).

Monneret, G., et al., "15R-Methyl-Prostaglandin $D_2$ Is a Potent and Selective CRTH2/$DP_2$ Receptor Agonist in Human Eosinophils," *The Journal of Pharmacology and Experimental Therapeutics* 304(1):349-355, The American Society for Pharmacology and Experimental Therapeutics, United States (2003).

Murray, J.J., et al., "Release of Prostaglandin $D_2$ Into Human Airways During Acute Antigen Challenge," *The New England Journal of Medicine* 315(1.3):800-804, Massachusetts Medical Society, United States (1986).

Sampson, S.E., et al., "Effect of inhaled prostaglandin $D_2$ in normal and atopic subjects, and of pretreatment with leukotriene $D_4$," *Thorax* 52:513-518, British Medical Assn, England (1997).

Stella, V.J., "Prodrugs as therapeutics," *Expert Opin. Ther. Patents* 14(3):277-280, Ashley Publications Ltd., United Kingdom (2004).

Testa, B., "Prodrug research: futile or fertile?" *Biochemical Pharmacology* 68:2097-2106, Elsevier Inc., United States (2004).

Dialog File 351, Accession No. 131699, Derwent WPI English language abstract for JP 43-24418.

PROCESS FOR THE PREPARATION OF 3-SUBSTITUTED (INDOL-1-YL)-ACETIC ACID ESTERS

The present invention relates to a process for the preparation of (5-halo-2-methyl-indol-1-yl)-acetic acid esters substituted at the 3-position with a —CH$_2$-aryl group and in particular to a high yielding process which is suitable for use on an industrial scale.

WO2005/044260 relates to compounds which are CRTH2 antagonists and which are therefore useful in the treatment of diseases and conditions mediated by the activity of PGD$_2$ at the CRTH2 receptor. Similar compounds are described in WO2006/095183, WO2008/012511 and WO2009/090414. All of the compounds exemplified in these documents are 5-halo-2-methyl indole-1-acetic acid derivatives with a —CH$_2$-aryl substituent at the 3-position. Several studies have been carried out on these compounds, including clinical trials in man, which have demonstrated that they are effective in treating allergic rhinitis and asthma, especially eosinophilic asthma and atopic asthma.

The indole acetic acid derivatives described in WO2005/044260, WO2006/095183, WO2008/012511 and WO2009/090414 can be obtained by hydrolysis of the equivalent alkyl or benzyl esters and such esters are also useful as prodrugs of the indole acetic acid compounds.

According to Example 1 of WO2005/044260, {3-[1-(4-chloro-phenyl)-ethyl]-5-fluoro-2-methyl-indol-1-yl}-acetic acid was prepared in the following steps:
i. (5-fluoro-2-methyl-indol-1-yl)-acetic acid ethyl ester and 4-acetylchlorobenzenze were reacted together in the presence of trifluoracetic acid and triethyl silane in the solvent 1,2-dichloroethane to give {3-[1-(4-chloro-phenyl)-ethyl]-5-fluoro-2-methyl-indol-1-yl}-acetic acid ethyl ester;
ii. the ester was hydrolysed using lithium hydroxide in a mixed tetrahydrofuran and water solvent to give the product.

Similar processes were used in WO2006/095183 and WO2008/012511.

WO2009/090414 relates to compounds of the general formula:

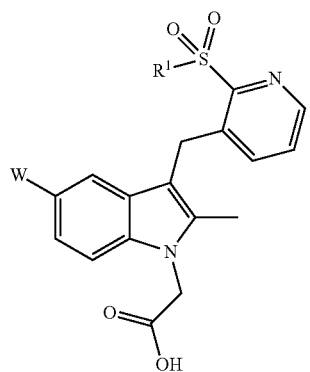

wherein
W is chloro or fluoro;
R$^1$ is phenyl optionally substituted with one or more substituents selected from halo, —CN, —C$_1$-C$_6$ alkyl, —SOR$^{3'}$, —SO$_2$R$^{3'}$, —SO$_2$N(R$^{2'}$)$_2$, —N(R$^{2'}$)$_2$, —NR$^{2'}$C(O)R$^{3'}$, —CO$_2$R$^{2'}$, —CONR$^{2'}$R$^{3'}$, —NO$_2$, —OR$^{2'}$, —SR$^{2'}$, —O(CH$_2$)$_p$OR$^{2'}$, and —O(CH$_2$)$_p$O(CH$_2$)$_q$OR$^{2'}$ wherein each R$^{2'}$ is independently hydrogen, —C$_1$-C$_6$ alkyl, —C$_3$-C$_8$ cycloalkyl, aryl or heteroaryl;

each R$^{3'}$ is independently, —C$_1$-C$_6$ alkyl, —C$_3$-C$_8$ cycloalkyl, aryl or heteroaryl;
p and q are each independently an integer from 1 to 3.

The process described in WO2009/090414 for the synthesis of these compounds is set out in Scheme 1 below, where R can be hydrogen, halo, —CN, —C$_1$-C$_6$ alkyl, —SOR$^{3'}$, —SO$_2$R$^{3'}$, —SO$_2$N(R$^{2'}$)$_2$, —N(R$^{2'}$)$_2$, —NR$^{2'}$C(O)R$^{3'}$, —CO$_2$R$^{2'}$, —CONR$^{2'}$R$^{3'}$, —NO$_2$, —OR$^{2'}$, —SR$^{2'}$, —O(CH$_2$)$_p$OR$^{2'}$, and —O(CH$_2$)$_p$O(CH$_2$)$_q$OR$^{2'}$ wherein R$^{2'}$ and R$^{3'}$ are as defined for the structure shown above. In particular, the document describes the synthesis of compounds in which R is H (Example 1), F (Example 2) or Cl (Example 3).

Scheme 1

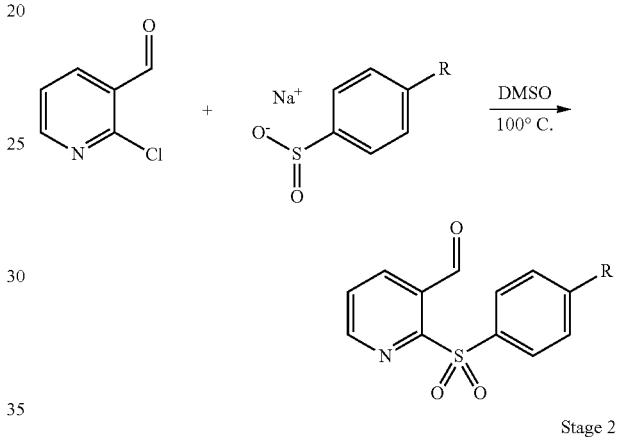

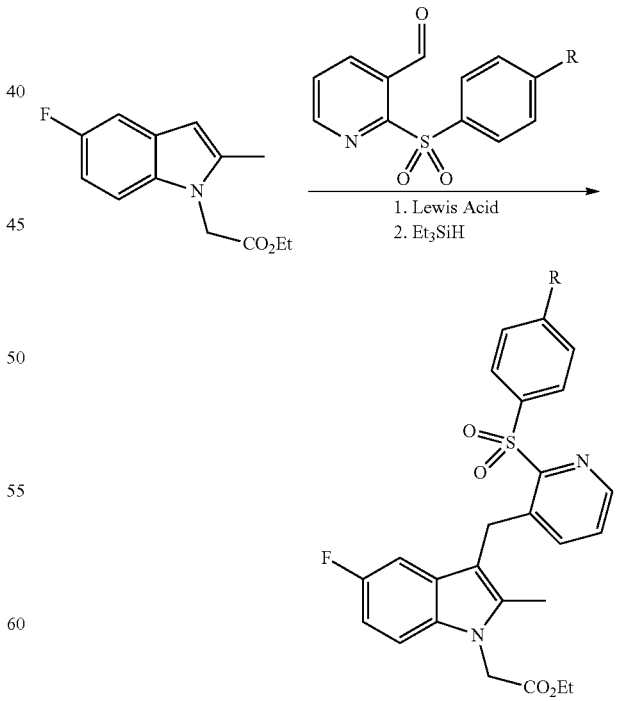

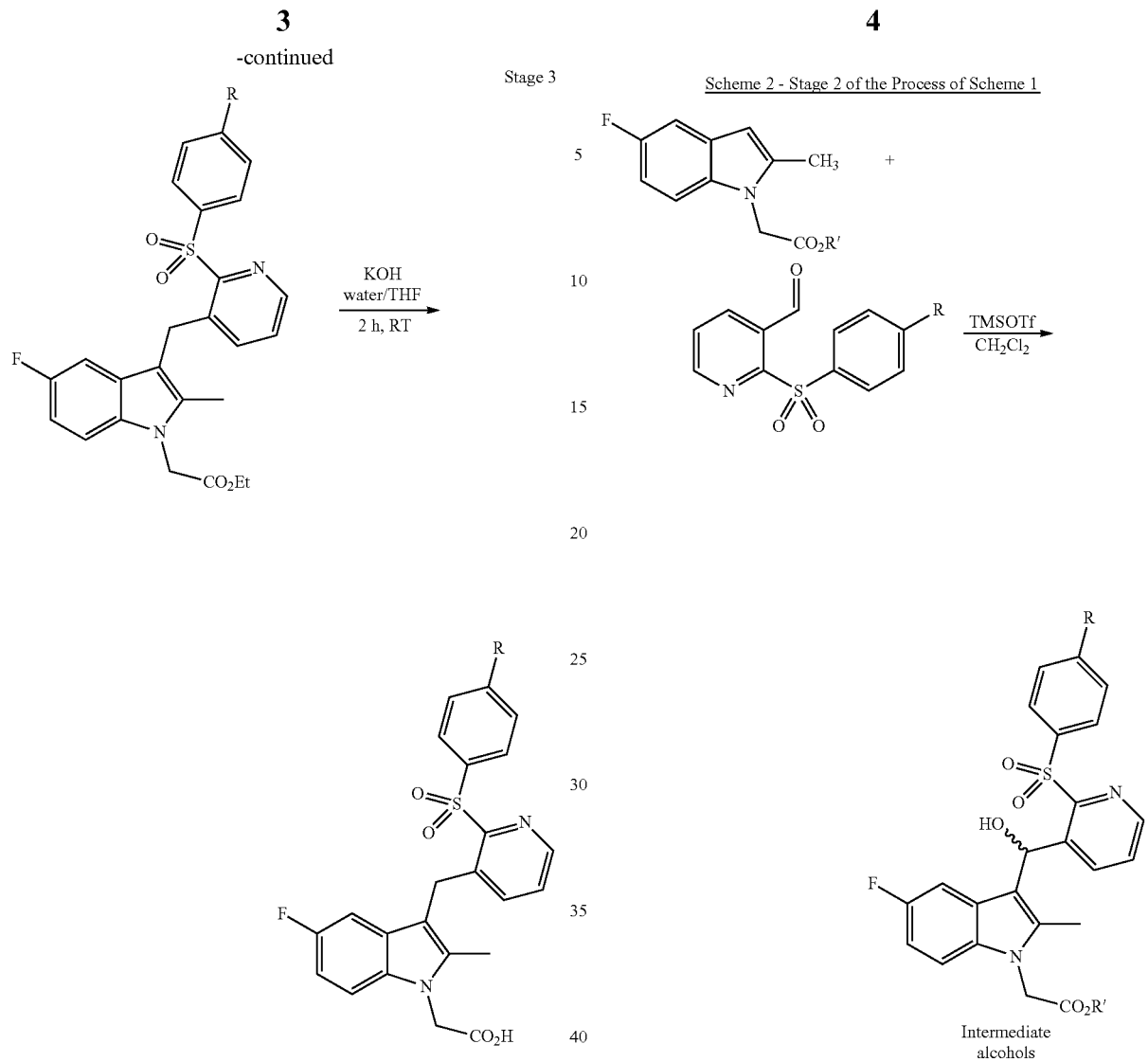

Scheme 2 - Stage 2 of the Process of Scheme 1

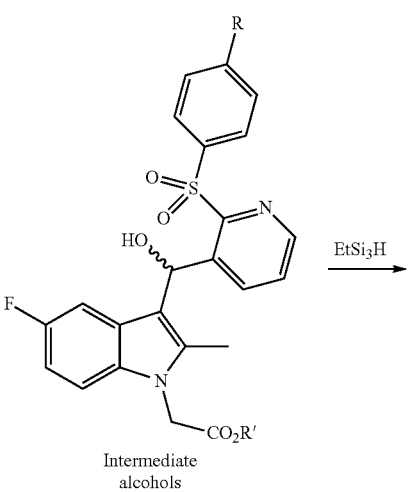

The route shown in Scheme 1 is essentially the same as the route used to prepare the compounds of WO2005/044260, WO2006/095183 and WO2008/012511. As can be seen from Scheme 1, the process has three stages and, in all cases, Stage 2 has proved to be particularly problematic.

In WO2005/044260, WO2006/095183 and WO2008/012511, Stage 2 was carried out in a single step by adding trifluoroacetic acid to a solution of the aldehyde, the indole ester and triethylsilane. However, although this process was suitable for the laboratory scale preparation of the compounds, it has proved to be unsuitable for use on an industrial scale because of the instability of intermediate alcohols generated during Stage 2. What is more, this process proved to be completely unsuitable for the production of the compounds described in WO2009/090414 because the majority of the product obtained in each case was a bis-indolyl product arising from further alkylation of an alcohol intermediate of the Stage 2 process.

Therefore, the Stage 2 process was adapted and the process described in WO2009/090414 differs from that described in the earlier documents in that the Lewis acid used was trimethylsilyltrifluoromethanesulfonate (TMSOTf) rather than trifluoroacetic acid. The Stage 2 process described in WO2009/090414 is illustrated in greater detail in Scheme 2, in which R is as defined above in Scheme 1 and R is $C_1$-$C_6$ alkyl or benzyl.

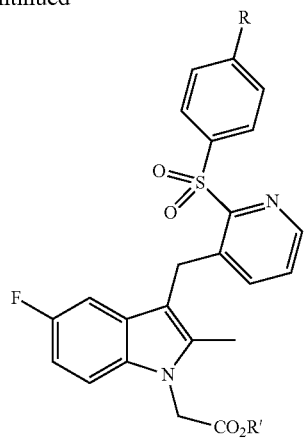

This process has been successfully used on a laboratory scale to produce the compounds described in WO2009/090414. However, attempts to scale up the process were less successful.

As with processes using other Lewis acids, the process set out in Scheme 2 tends to give rise to a bis-indolyl impurity of the formula:

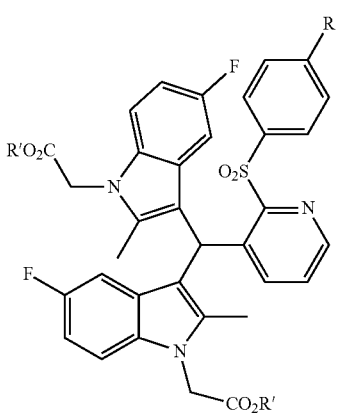

where R is as defined in Scheme 1 and R' is $C_1$-$C_6$ alkyl or benzyl.

The authors of WO2009/090414 were able to minimise amounts of this impurity by use of an aqueous work-up and by conducting the reaction at very high dilution. However, these solutions are not appropriate for an industrial scale process. In particular, the ratio of starting material to solvent used in the process described in WO2009/090414 is about 1:50 w/vol and dilutions of this order are simply not viable on an industrial scale.

When the inventors attempted to conduct the reaction at a more industrially acceptable concentration of between about 1:10 and 1:15 w/vol, it was found that the intermediate alcohol precipitated as a gummy material which agglomerated on the stirrer blade and which could lead to equipment damage at larger scales. At the higher dilution used in WO2009/090414, the insoluble intermediate alcohol was still present but did not agglomerate on the stirrer.

The inventors therefore attempted the Stage 2 reaction at concentrations of between about 1:10 and 1:15 w/vol using a number of alternative Lewis acids including trifluoroacetic acid, trifluoromethanesulfonic acid, boron trifluoride, aluminium trichloride and zinc dibromide. However, all of these Lewis acids either gave rise to an unacceptably high level of the bis-indolyl impurity shown above or to a gummy agglomerate of the intermediate alcohol similar to that obtained with TMSOTf. Surprisingly, however, the inventors have found that, unlike all of the other Lewis acids tested, titanium tetrachloride (TiCl$_4$) did give acceptable results in the reductive alkylation stage.

Therefore, in a first aspect of the invention there is provided a process for the preparation of a compound of general formula (I):

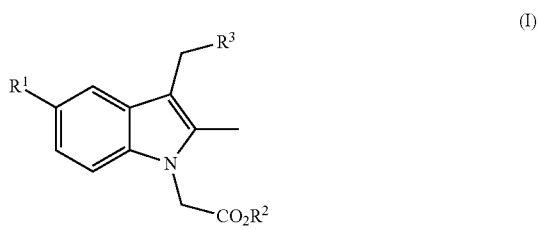

wherein $R^1$ is fluoro, chloro or bromo;
$R^2$ is $C_1$-$C_6$ alkyl or benzyl; and
$R^3$ is aryl or heteroaryl optionally substituted with one or more substituents selected from halo, OH, CN, $R^4$, $COR^4$, $CH_2R^4$, $OR^4$, $SR^4$, $SO_2R^4$ or $SO_2YR^4$;
$R^4$ is $C_1$-$C_6$ alkyl, $C_3$-$C_8$ cycloalkyl, heterocyclyl, aryl or heteroaryl, any of which may optionally be substituted with one or more substituents selected from halo, OH, CN, $NO_2$, $C_1$-$C_6$ alkyl or $O(C_1$-$C_6$ alkyl); and
Y is NH or a straight or branched $C_1$-$C_4$ alkylene chain;
the process comprising:
i. reacting a compound of general formula (II):

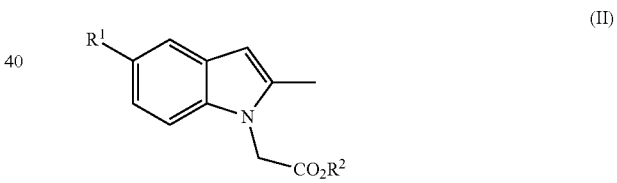

wherein $R^1$ and $R^2$ are as defined for general formula (I);
with a compound of general formula (III)

wherein $R^3$ is as defined for general formula (I);
in a suitable solvent and in the presence of titanium tetrachloride, wherein the ratio of the compound of general formula (II) to solvent is from 1:8 to 1:20 weight/volume; and
ii. reacting the product of step (i) with a reducing agent to give a compound of general formula (I).

The inventors have found that when the reaction is conducted using TiCl$_4$ as the Lewis acid, the product of step (i) precipitates as a solid but forms a suspension rather than a gum and therefore does not agglomerate on the stirrer, even though the amount of solvent used is significantly lower than for processes employing trifluoroacetic acid or trimethylsilyl triflate. Furthermore, the amount of the bis-indolyl impurity which arises from the reaction of a further molecule of the compound of general formula (II) with the product of step (i), is kept to an acceptable level. These findings were surprising as they differed from the results with the other Lewis acids tested.

The inventors have attempted to rationalise the reasons for the success of TiCl$_4$ as a Lewis acid for this process by considering more fully the reaction of the compound of general formula (II) with the compound of general formula (III).

In the past, when the reaction has been conducted using a protic acid such as trifluoroacetic acid, it has been suggested that it proceeds via the reaction shown in Scheme 3.

As explained above, the bis-indolyl compound (IVc) has proved to be a major product with the majority of Lewis acids, although the proportions of compounds of formulae (I) and (IVc) will vary depending upon the particular target compound of general formula (I).

As shown in Scheme 3, the compound of general formula (II) reacts with the compound of general formula (III) in the presence of a Lewis acid to give an intermediate alcohol of general formula (IVa). The intermediate alcohol is in equilibrium with the intermediate of general formula (IVb), which can either react with a reducing agent to give the compound of general formula (I) or, alternatively, may react with an additional molecule of the compound of general formula (II) to give a bis-indolyl compound of general formula (IVc).

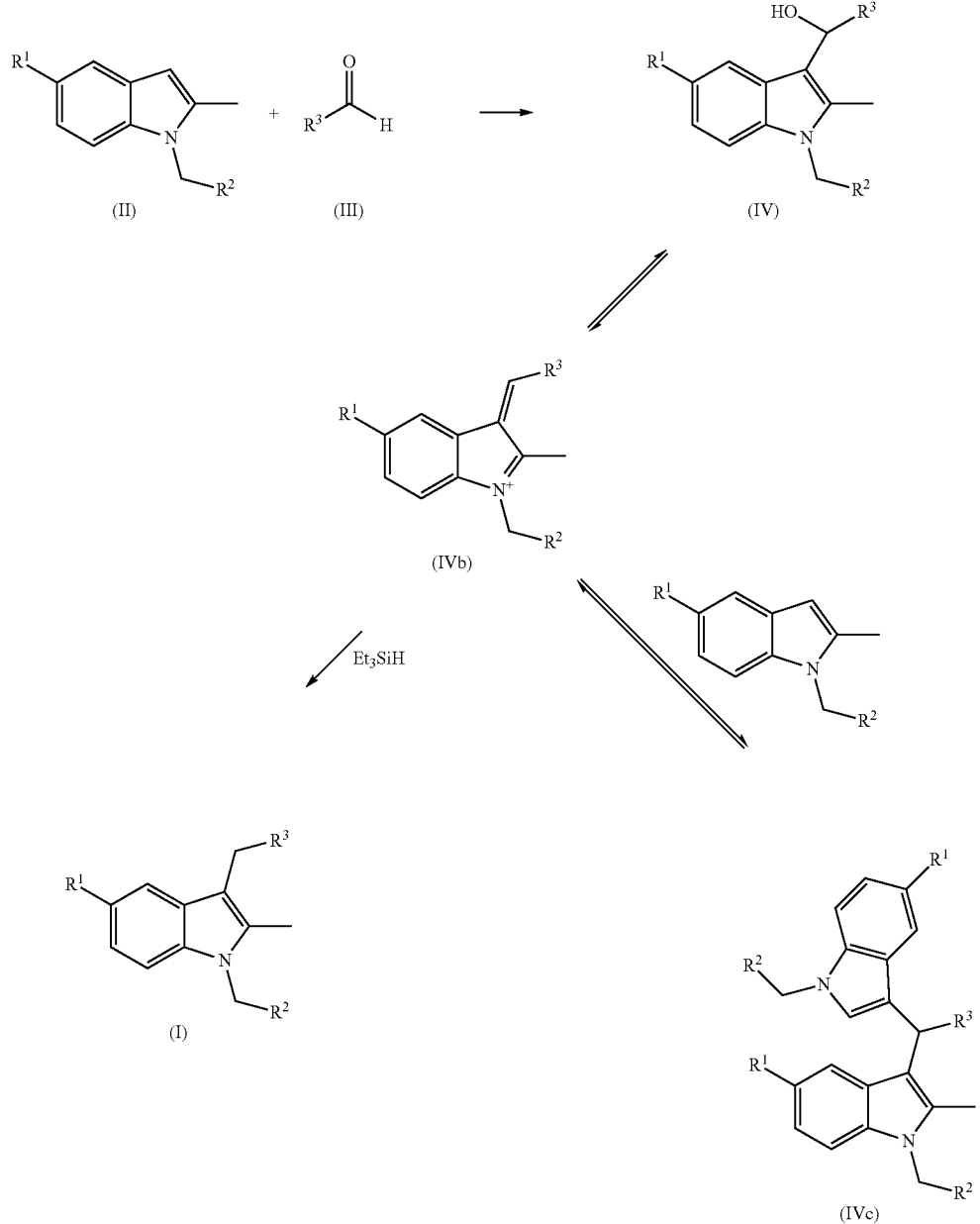

Scheme 3

The bis-indolyl compound of general formula (IVc) is in equilibrium with the intermediate of general formula (IVb) and therefore it has proved possible in some cases, for example using a non protic Lewis acid such as TMSOTf, to convert the bis-indolyl compound to the intermediates of general formula (IVb) and (IVa) and the starting material of formula (II) by the addition of a small amount of water, for example about 1 equivalent, at the end of the reduction.

Surprisingly, however, when $TiCl_4$ is used as the Lewis acid it is not necessary to add water to remove the bis-indolyl product and the inventors have therefore speculated that, the reaction may proceed via different intermediates instead of or in addition to the intermediates of general formula (IVa) and (IVb), perhaps resulting from the addition of Cl— rather than OH—. Thus, possible intermediates may have the structure:

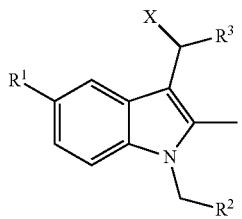

Where X can be, for example Cl or a titanium based moiety.

The product of step (i) of the process of the invention is not clear but it is possible that the presence of alternative intermediates may be the reason that the product of step (i) forms a suspension rather than agglomerating on the stirrer as with other Lewis acids. However, this is a theory only and the effectiveness of the process of the invention is not dependent on its being correct.

In the present specification "$C_1$-$C_6$ alkyl" refers to a straight or branched saturated hydrocarbon chain having one to six carbon atoms and optionally substituted with with one or more $C_3$-$C_7$ cycloalkyl groups. Examples include methyl, ethyl, n-propyl, isopropyl, t-butyl, n-hexyl, methylenecyclopropyl, methylenecyclobutyl, and methylenecyclopentyl.

"$C_1$-$C_4$ alkyl" and "$C_1$-$C_{18}$ alkyl" have similar meanings except that they contain from one to four and from one to eighteen carbon atoms respectively.

$C_3$-$C_7$ cycloalkyl refers to a saturated 3 to 7 membered carbocyclic ring. Examples of such groups include cyclopropyl, cyclobutyl, cyclopentyl and cyclohexyl.

The term "$C_1$-$C_4$ alkylene" in the context of the present specification refers to a disubstituted straight or branched saturated hydrocarbon chain having one to four carbon atoms.

In the present specification, "halo" refers to fluoro, chloro, bromo or iodo.

The term "aryl" in the context of the present specification refers to an aromatic ring system having from 5 to 14 ring carbon atoms and containing up to three rings. Examples of aryl groups are benzene and naphthalene.

The term "heteroaryl" in the context of the specification refers to a ring system with aromatic character having from 5 to 14 ring atoms, at least one of which is a heteroatom selected from N, O and S, and containing up to three rings. Where a heteroaryl group contains more than one ring, not all rings must be fully aromatic in character. Rings which are not fully aromatic may be substituted with one or more oxo groups. Examples of heteroaryl groups include pyrrole, thiophene, thiazole, pyridine, pyrimidine, indole, benzofuran, benzimidazole, tetrahydroquinoline, indoline, quinoline, isoquinoline, quinoxaline, imidazo[1,2-a]pyridine and pyrazolo[1,5-a]pyridine.

The term "heterocyclyl" in the context of the specification refers to a saturated ring system having from 4 to 8 ring atoms, at least one of which is a heteroatom selected from N, O and S and which may be optionally substituted by one or more oxo groups. Examples of heterocyclyl groups include azetidinyl, piperidinyl; tetrahydrofuranyl, tetrahydropyranyl, dioxanyl, thiomorpholinyl, 1,1-dioxo-1λ6-thiomorpholinyl, morpholinyl, pyrrolyl, piperizinyl, azepanyl, 1,4-diazepanyl, 1,4-oxazepanyl and azocanyl.

If a chiral centre or another form of isomeric centre is present in a compound of the present invention, all forms of such isomer or isomers, including enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

Suitable compounds which may be prepared by the process of the invention are those in which, independently or in any combination:

$R^1$ is fluoro;

$R^2$ is $C_1$-$C_4$ alkyl; and $R^3$ is quinoline, quinoxaline, isoquinoline, thiazole, phenyl, naphthalene, thiophene, pyrrole or pyridine, any of which may optionally be substituted as set out above.

More suitably, $R^2$ is methyl or ethyl, especially ethyl.

More typical $R^3$ groups include optionally substituted quinoline, phenyl, naphthalene, thiophene, pyrrole or pyridine.

When $R^3$ is quinoline or isoquinoline, it is suitably unsubstituted or substituted with one or more halo substituents, especially fluoro.

When $R^3$ is phenyl, naphthalene, thiophene, pyrrole or pyridine, it may optionally have one or more substituents, with particularly suitable substituents including $OR^4$, $SO_2R^4$ or $SO_2YR^4$; where $R^4$ and Y are as defined above.

Typically, in this case, $R^4$ is $C_1$-$C_6$ alkyl, a 4- to 6-membered cycloalkyl group, a 5- or 6-membered heterocyclyl group or phenyl, any of which may be substituted as defined above.

When $R^3$ is pyridyl it is most suitably a 3-pyridyl moiety.

In more active compounds, Y, when present, is a $CH_2$ moiety.

When $R^3$ is substituted with $SO_2R^4$ or $SO_2YR^4$, the $R^4$ group is generally unsubstituted or substituted with one or more substituents chosen from methyl and halo, particularly chloro or fluoro.

When $R^3$ is substituted with $OR^4$, the $R^4$ group may be unsubstituted or substituted with one or more substituents chosen from halo, cyano, $C_1$-$C_4$ alkyl and $O(C_1$-$C_4$ alkyl).

The process of the present invention is particularly suitable for the preparation of compounds of formula (Ia):

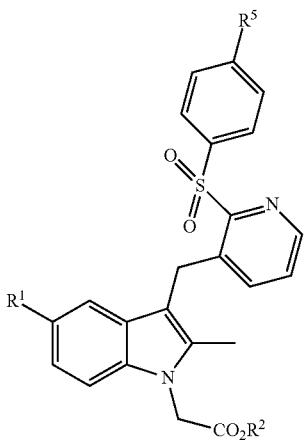

(Ia)

wherein R¹ and R² are as defined above for general formula (I);
R⁵ is hydrogen halo, —CN, —$C_1$-$C_6$ alkyl, —$SOR^7$, —$SO_2R^7$, —$SO_2N(R^6)_2$, —$N(R^6)_2$, —$NR^6C(O)R^7$, —$CO_2R^6$, —$CONR^6R^7$, —$NO_2$, —$OR^6$, —$SR^6$, —$O(CH_2)_p$ $OR^6$, and —$O(CH_2)_pO(CH_2)_qOR^6$ wherein
each $R^6$ is independently hydrogen, —$C_1$-$C_6$ alkyl, —$C_3$-$C_8$ cycloalkyl, aryl or heteroaryl;
each $R^7$ is independently, —$C_1$-$C_6$ alkyl, —$C_3$-$C_8$ cycloalkyl, aryl or heteroaryl;
p and q are each independently an integer from 1 to 3.

Compounds of general formula (Ia) have proved particularly difficult to make, with attempts using TFA being not synthetically useful and the use of TMSOTf requiring very high dilution of the reaction mixture in order to give the desired product.

Particularly suitable compounds of formula (Ia) are those in which, independently or in combination:
R¹ is fluoro; and
R² is $C_1$-$C_4$ alkyl, more usually methyl or ethyl and especially ethyl.

Suitably, in compounds of formula (Ia), R⁵ is hydrogen or halo, more suitably hydrogen, fluoro or chloro.

Compounds of general formula (I) which may be prepared by the process of the invention include the $C_1$-$C_6$ alkyl or benzyl esters of:
{3-[1-(4-Chloro-phenyl)-ethyl]-5-fluoro-2-methyl-indol-1-yl}-acetic acid;
{5-Fluoro-2-methyl-3-[1-(4-trifluoromethyl-phenyl)-ethyl]-indol-1-yl}-acetic acid;
{3-[1-(4-tert-Butyl-phenyl)-ethyl]-5-fluoro-2-methyl-indol-1-yl}-acetic acid;
{5-Fluoro-3-[1-(4-methanesulfonyl-phenyl)-ethyl]-2-methyl-indol-1-yl}-acetic acid;
[5-Fluoro-2-methyl-3-(1-naphthalen-2-yl-ethyl)-indol-1-yl]-acetic acid;
(5-Fluoro-2-methyl-3-quinolin-2-ylmethyl-indol-1-yl)-acetic acid;
(5-Fluoro-2-methyl-3-naphthalen-2-ylmethyl-indol-1-yl)-acetic acid;
[5-Fluoro-3-(8-hydroxyquinolin-2-ylmethyl)-2-methyl-indol-1-yl]-acetic acid;
[5-Fluoro-2-methyl-3-(quinoxalin-2-ylmethyl)indol-1-yl]-acetic acid;
[5-Fluoro-3-(4-methoxy-benzyl)-2-methyl-indol-1-yl]-acetic acid;
[5-Fluoro-2-methyl-3-(1,3-thiazol-2-ylmethyl)indol-1-yl]-acetic acid;
[3-(4-Chloro-benzyl)-5-fluoro-2-methyl-indol-1-yl]-acetic acid;
[5-Fluoro-2-methyl-3-(4-trifluoromethyl-benzyl)-indol-1-yl]-acetic acid;
[5-Fluoro-2-methyl-3-(4-tert-butyl-benzyl)-indol-1-yl]-acetic acid;
{5-Fluoro-2-methyl-3-[(4-phenylphenyl)methyl]indol-1-yl}-acetic acid;
[5-Fluoro-3-(4-methanesulfonyl-benzyl)-2-methyl-indol-1-yl]-acetic acid;
{5-Fluoro-3-[(6-fluoroquinolin-2-yl)methyl]-2-methylindol-1-yl}-acetic acid;
(2-Methyl-3-quinolin-2-ylmethyl-indol-1-yl)-acetic acid;
(5-Chloro-2-methyl-3-quinolin-2-ylmethyl-indol-1-yl)-acetic acid;
(3-{[1-(Benzenesulfonyl)pyrrol-2-yl]methyl}-5-fluoro-2-methylindol-1-yl)-acetic acid;
[5-Fluoro-2-methyl-3-({1-[(4-methylbenzene)sulfonyl]pyrrol-2-yl}methyl)indol-1-yl]-acetic acid;
[3-({1-[(2,4-Difluorobenzene)sulfonyl]pyrrol-2-yl}methyl)-5-fluoro-2-methylindol-1-yl]-acetic acid;
(3-{[2-(Benzenesulfonyl)phenyl]methyl}-5-fluoro-2-methylindol-1-yl)-acetic acid;
[3-({2-[(4-Chlorobenzene)sulfonyl]phenyl}methyl)-5-fluoro-2-methylindol-1-yl]-acetic acid;
[5-Fluoro-3-({2-[(4-fluorobenzene)sulfonyl]phenyl}methyl)-2-methylindol-1-yl]-acetic acid;
(3-{[2-(Benzenesulfonyl)pyridin-3-yl]methyl}-5-fluoro-2-methylindol-1-yl)-acetic acid;
[5-Fluoro-3-({2-[(4-fluorobenzene)sulfonyl]pyridin-3-yl}methyl)-2-methylindol-1-yl]-acetic acid;
[3-({2-[(4-Chlorobenzene)sulfonyl]pyridin-3-yl}methyl)-5-fluoro-2-methylindol-1-yl]-acetic acid;
2-(3-(4-(Benzylsulfonyl)benzyl)-5-fluoro-2-methyl-indol-1-yl)-acetic acid;
2-(3-(4-(4-Chlorobenzylsulfonyl)benzyl)-5-fluoro-2-methyl-indol-1-yl)-acetic acid;
2-(3-(3-(Benzylsulfonyl)benzyl)-5-fluoro-2-methyl-indol-1-yl)-acetic acid;
2-(5-Fluoro-3-(3-(4-fluorobenzylsulfonyl)benzyl)-2-methyl-indol-1-yl)-acetic acid;
2-(3-(2-(Benzylsulfonyl)benzyl)-5-fluoro-2-methyl-indol-1-yl)-acetic acid;
2-(3-(4-(4-Fluorobenzylsulfonyl)benzyl)-5-fluoro-2-methyl-indol-1-yl)-acetic acid;
2-(3-(2-(Cyclohexylsulfonyl)benzyl)-5-fluoro-2-methyl-indol-1-yl)-acetic acid;
2-(5-Fluoro-2-methyl-3-(2-(piperidin-1-ylsulfonyl)benzyl)-indol-1-yl)-acetic acid;
2-(3-(2-(Cyclopentylsulfonyl)benzyl)-5-fluoro-2-methyl-indol-1-yl)-acetic acid;
2-(5-Fluoro-2-methyl-3-(3-(piperidin-1-ylsulfonyl)benzyl)-indol-1-yl)-acetic acid;
2-(5-Fluoro-2-methyl-3-(2-(pyrrolidin-1-ylsulfonyl)benzyl)-indol-1-yl)-acetic acid;
2-(3-(4-(Cyclohexylsulfonyl)benzyl)-5-fluoro-2-methyl-indol-1-yl)-acetic acid;
2-(3-(4-(Cyclopentylsulfonyl)benzyl)-5-fluoro-2-methyl-indol-1-yl)-acetic acid;
2-(3-(2-(Cyclobutylsulfonyl)benzyl)-5-fluoro-2-methyl-indol-1-yl)-acetic acid;
2-(5-Fluoro-2-methyl-3-(3-(pyrrolidin-1-ylsulfonyl)benzyl)-indol-1-yl)-acetic acid;
2-(5-Fluoro-2-methyl-3-(4-(piperidin-1-ylsulfonyl)benzyl)-indol-1-yl)-acetic acid;

[5-Fluoro-2-methyl-3-(2-phenoxybenzyl)-indol-1-yl]-acetic acid;
[5-Fluoro-2-methyl-3-(2-(4-methoxyphenoxy)benzyl)-indol-1-yl]-acetic acid;
[5-Fluoro-2-methyl-3-(2-(4-methylphenoxy)benzyl)-indol-1-yl]-acetic acid;
[5-Fluoro-2-methyl-3-(2-(2,4-dichlorophenoxy)benzyl)-indol-1-yl]-acetic acid;
[5-Fluoro-2-methyl-3-(2-(4-fluorophenoxy)benzyl)-indol-1-yl]-acetic acid;
[5-Fluoro-2-methyl-3-(2-(3,4-difluorophenoxy)benzyl)-indol-1-yl]-acetic acid;
[5-Fluoro-2-methyl-3-(2-(4-cyanophenoxy)benzyl)-indol-1-yl]-acetic acid;
[5-Fluoro-2-methyl-3-(2-(4-chlorophenoxy)benzyl)-indol-1-yl]-acetic acid;
[5-Fluoro-2-methyl-3-(2-(2-cyanophenoxy)benzyl)-indol-1-yl]-acetic acid;
(5-Fluoro-2-methyl-3-{[2-(4-methylphenoxy)pyridin-3-yl]methyl}indol-1-yl)-acetic acid;
{5-Fluoro-3-[(3-methanesulfonylnaphthalen-2-yl)methyl]-2-methylindol-1-yl}-acetic acid;
{5-Fluoro-3-[(1-methanesulfonylnaphthalen-2-yl)methyl]-2-methylindol-1-yl}-acetic acid;
{5-Fluoro-3-[(6-methanesulfonylnaphthalen-2-yl)methyl]-2-methylindol-1-yl}-acetic acid;
[5-Fluoro-2-methyl-3-(quinolin-3-ylmethyl)indol-1-yl]-acetic acid;
[5-Fluoro-2-methyl-3-(quinoxalin-6-ylmethyl)indol-1-yl]-acetic acid;
[5-Fluoro-2-methyl-3-(quinolin-7-ylmethyl)indol-1-yl]-acetic acid;
{5-Fluoro-3-[(6-methanesulfonylquinolin-2-yl)methyl]-2-methylindol-1-yl}-acetic acid;
{5-Fluoro-3-[(4-methanesulfonylquinolin-2-yl)methyl]-2-methylindol-1-yl}-acetic acid;
(5-Fluoro-2-methyl-3-{pyrazolo[1,5-a]pyridin-3-ylmethyl}indol-1-yl)-acetic acid;
(5-Fluoro-3-{imidazo[1,2-a]pyridin-2-ylmethyl}-2-methyl-indol-1-yl)-acetic acid;
(5-Fluoro-2-methyl-3-{[2-(methylsulfanyl)phenyl]methyl}indol-1-yl)-acetic acid;
(5-Fluoro-2-methyl-3-{[3-(methylsulfanyl)phenyl]methyl}indol-1-yl)-acetic acid;
(5-Fluoro-2-methyl-3-{[4-(ethylsulfanyl)phenyl]methyl}indol-1-yl)-acetic acid(3-{[4-(Ethylsulfanyl)phenyl]methyl}-5-fluoro-2-methylindol-1-yl)-acetic acid;
(5-Fluoro-2-methyl-3-{[4-(n-propylsulfanyl)phenyl]methyl}indol-1-yl)-acetic acid;
(5-Fluoro-2-methyl-3-{[4-(i-propylsulfanyl)phenyl]methyl}indol-1-yl)-acetic acid;
(5-Fluoro-2-methyl-3-{[4-(t-butylsulfanyl)phenyl]methyl}indol-1-yl)-acetic acid;
(5-Fluoro-2-methyl-3-{[4-(pentan-3-ylsulfanyl)phenyl]methyl}indol-1-yl)-acetic acid;
[3-({4-[(Cyclopropylmethyl)sulfanyl]phenyl}methyl)-5-fluoro-2-methylindol-1-yl]-acetic acid;
{3-[(4,4-Dimethyl-2,3-dihydro-1-benzothiopyran-6-yl)methyl]-5-fluoro-2-methylindol-1-yl}-acetic acid;
(3-{[2-(Ethanesulfonyl)phenyl]methyl}-5-fluoro-2-methyl-indol-1-yl)-acetic acid;
(5-Fluoro-2-methyl-3-{[2-(propane-1-sulfonyl)phenyl]methyl}indol-1-yl)-acetic acid;
(5-Fluoro-2-methyl-3-{[2-(propane-2-sulfonyl)phenyl]methyl}indol-1-yl)-acetic acid;
(3-{[2-(Butane-1-sulfonyl)phenyl]methyl}-5-fluoro-2-methylindol-1-yl)-acetic acid;
(3-{[2-(Butane-2-sulfonyl)phenyl]methyl}-5-fluoro-2-methylindol-1-yl)-acetic acid;
(5-Fluoro-2-methyl-3-{[2-(2-methylpropane-2-sulfonyl)phenyl]methyl}indol-1-yl)-acetic acid;
(5-Fluoro-2-methyl-3-{[2-(pentane-1-sulfonyl)phenyl]methyl}indol-1-yl)-acetic acid;
(3-{[2-(Cyclopropylmethane)sulfonylphenyl]methyl}-5-fluoro-2-methylindol-1-yl)-acetic acid;
(5-Fluoro-2-methyl-3-{[2-(propylsulfamoyl)phenyl]methyl}indol-1-yl)-acetic acid;
(3-{[2-(Butylsulfamoyl)phenyl]methyl}-5-fluoro-2-methyl-indol-1-yl)-acetic acid;
(5-Fluoro-2-methyl-3-{[3-(propylsulfamoyl)phenyl]methyl}indol-1-yl)-acetic acid;
(3-{[3-(Butylsulfamoyl)phenyl]methyl}-5-fluoro-2-methyl-indol-1-yl)-acetic acid;
(5-Fluoro-2-methyl-3-{[4-(trifluoromethane)sulfonylphenyl]methyl}indol-1-yl)-acetic acid;
(3-{[4-(Ethanesulfonyl)phenyl]methyl}-5-fluoro-2-methyl-indol-1-yl)-acetic acid;
(5-Fluoro-2-methyl-3-{[4-(propane-1-sulfonyl)phenyl]methyl}indol-1-yl)-acetic acid;
(5-Fluoro-2-methyl-3-{[4-(propane-2-sulfonyl)phenyl]methyl}indol-1-yl)-acetic acid;
(3-{[4-(Butane-1-sulfonyl)phenyl]methyl}-5-fluoro-2-methylindol-1-yl)-acetic acid;
(5-Fluoro-2-methyl-3-{[4-(2-methylpropane-2-sulfonyl)phenyl]methyl}indol-1-yl)-acetic acid;
(5-Fluoro-2-methyl-3-{[4-(pentane-1-sulfonyl)phenyl]methyl}indol-1-yl)-acetic acid;
(5-Fluoro-2-methyl-3-{[4-(pentan-3-ylsulfonyl)phenyl]methyl}indol-1-yl)-acetic acid;
[3-({4-[(Cyclopropylmethyl)sulfonyl]phenyl}methyl)-5-fluoro-2-methylindol-1-yl]-acetic acid;
(5-Fluoro-2-methyl-3-{[4-(propylsulfamoyl)phenyl]methyl}indol-1-yl)-acetic acid;
(3-{[4-(Butylsulfamoyl)phenyl]methyl}-5-fluoro-2-methyl-indol-1-yl)-acetic acid;
(5-Fluoro-2-methyl-3-{[4-(trifluoromethoxy)phenyl]methyl}indol-1-yl)-acetic acid;
(5-Fluoro-3-{[4-methanesulfonyl-3-(trifluoromethyl)phenyl]methyl}-2-methylindol-1-yl)-acetic acid;
(5-Fluoro-3-{[4-methanesulfonyl-3-(trifluoromethoxy)phenyl]methyl}-2-methylindol-1-yl)-acetic acid;
{5-Fluoro-3-[(5-methanesulfonylthiophen-2-yl)methyl]-2-methylindol-1-yl}-acetic acid;
{3-[(4,4-dimethyl-1,1-dioxo-2,3-dihydro-1$\lambda^6$-benzothiopyran-6-yl)methyl]-5-fluoro-2-methylindol-1-yl}-acetic acid;
[3-({1-[(4-Chlorobenzene)sulfonyl]pyrrol-2-yl}methyl)-5-fluoro-2-methylindol-1yl]-acetic acid;
[5-Fluoro-3-({1-[(4-fluorobenzene)sulfonyl]pyrrol-2-yl}methyl)-2-methylindol-1-yl]-acetic acid;
[5-Fluoro-3-({1-[(4-methoxybenzene)sulfonyl]pyrrol-2-yl}methyl)-2-methylindol-1-yl]-acetic acid;
{3-[1-(2,4-Dichloro-benzenesulfonyl)pyrrol-2-ylmethyl]-5-fluoro-2-methyl-indol-1-yl}-acetic acid;
[5-Fluoro-3-({1-[(4-methanesulfonylbenzene)sulfonyl]pyrrol-2-yl}methyl)-2-methylindol-1-yl]-acetic acid;
{5-Fluoro-2-methyl-3-[(2-phenylphenyl)methyl]indol-1-yl}-acetic acid;
(3-{[1-(Benzenesulfonyl)indol-2-yl]methyl}-5-fluoro-2-methylindol-1-yl)-acetic acid;
(3-{[2-(4-Chlorophenyl)phenyl]methyl}-5-fluoro-2-methylindol-1-yl)-acetic acid;
(5-Fluoro-2-methyl-3-{[2-(4-methylphenyl)phenyl]methyl}indol-1-yl)-acetic acid;

{5-Fluoro-2-methyl-3-[(3-phenoxyphenyl)methyl]indol-1-yl}-acetic acid;
[5-Fluoro-3-({4-[(4-fluorophenyl)carbonyl]-1-methylpyrrol-2-yl}methyl)-2-methylindol-1-yl]-acetic acid;
{5-Fluoro-2-methyl-3-[(6-{[3-(trifluoromethyl)phenyl]methyl}pyridin-3-yl)methyl]indol-1-yl}-acetic acid;
{5-Fluoro-2-methyl-3-[(3-phenoxythiophen-2-yl)methyl]indol-1-yl}-acetic acid;
(3-{[2-(Benzenesulfonyl)-1,3-thiazol-5-yl]methyl}-5-fluoro-2-methylindol-1-yl)-acetic acid;
{3-[(1-Benzylpyrazol-4-yl)methyl]-5-fluoro-2-methyl indol-1-yl}-acetic acid;
(3-{[5-(4-Chlorophenoxy)-1-methyl-3-(trifluoromethyl)pyrazol-4-yl]methyl}-5-fluoro-2-methylindol-1-yl)-acetic acid;
[3-({5-[(4-Chlorobenzene)sulfonyl]furan-2-yl}methyl)-5-fluoro-2-methylindol-1-yl]-acetic acid;
[3-({5-[(4-Chlorobenzene)sulfonyl]thiophen-2-yl}methyl)-5-fluoro-2-methylindol-1-yl]-acetic acid;
[3-({3-[(4-Chlorobenzene)sulfonyl]thiophen-2-yl}methyl)-5-fluoro-2-methylindol-1-yl]-acetic acid;
{3-[(2-Benzylphenyl)methyl]-5-fluoro-2-methylindol-1-yl}-acetic acid;
with the ethyl esters of the above compounds being particularly suitable for preparation by this process.

Among the compounds listed above, the process is particularly suitable for the preparation of esters of the compounds of general formula (Ia), namely the $C_1$-$C_6$ alkyl and benzyl esters of:
(3-{[2-(Benzenesulfonyl)pyridin-3-yl]methyl}-5-fluoro-2-methylindol-1-yl)-acetic acid;
[5-Fluoro-3-({2-[(4-fluorobenzene)sulfonyl]pyridin-3-yl}methyl)-2-methylindol-1-yl]-acetic acid;
[3-({2-[(4-Chlorobenzene)sulfonyl]pyridin-3-yl}methyl)-5-fluoro-2-methylindol-1-yl]-acetic acid;
and in particular the ethyl esters of these compounds.

Suitable solvents for the process include, in particular halogenated solvents, for example chlorinated solvents such as chloroform, 1,2-dichloroethane and especially dichloromethane.

The ratio of the compound of general formula (II) to solvent is more suitably from 1:10 to 1:15, for example 1:10 to 1:12 and typically about 1:12 weight/volume.

The solvent ratio refers to the total amount of solvent used in step (i) and includes for example, any solvent in which the titanium tetrachloride is added; any solvent in which the compounds of general formula (II) and general formula (III) are dissolved and any solvent added to the reaction vessel for washing or further dilution.

Furthermore, it has been possible to optimise the reaction so that the purity of the product is at least 95% area or, when expressed in weight percentage terms, at least 95% w/w. The reaction was devised in order to give a product in which the amount of bis-indolyl impurity formed is 55% area by HPLC and in some cases ≤2% area by HPLC. The inventors have obtained a product containing less than 0.5% w/w of the bis-indolyl impurity and less than 0.5% w/w of the alcohol intermediate. The yield is also greatly improved in comparison with previous processes for the preparations of these compounds; using the process of the invention, it has proved possible to obtain the product in a yield of at least about 75%. In some cases, the yield is even higher, for example at least about 80% or at least about 85%.

One way of adjusting the amount of the bis-indolyl impurity in the final product is to adjust the molar ratio of titanium tetrachloride to the compound of formula (II). This is typically from 1:1 to 3:1, more usually from 1.1:1 to 2.5:1.

It is advantageous from the point of view of cost to keep the amount of titanium tetrachloride to a minimum but it has been found that an increase in the stoichiometry of the titanium tetrachloride from 1.1:1 to 2:1 reduces the amount of bis-indolyl impurity formed from about 20% area to under 10% area. Therefore it is preferred that the molar ratio of titanium tetrachloride to compound of general formula (II) is from about 1.8:1 to 2.2:1, usually about 2:1.

The amount of bis-indolyl impurity can also be reduced by conducting the reaction of step (i) at an appropriate temperature and then maintaining it at this temperature for an appropriate time after the addition of the compounds of formulae (II) and (III).

Typically, the reaction is conducted at a temperature of −10 to 25° C., more usually at room temperature, for example about 20° C. The bis-indolyl impurity is in equilibrium with the intermediates and the starting material of general formula (II) and the inventors have found that at a temperature of 20° C. the reverse reaction leading from the bis-indolyl impurity to the starting material and the intermediates is favoured such that after a prolonged period of stirring at a suitable temperature, in combination with a suitable stoichiometric ratio of $TiCl_4$ to compound of formula (II), the level of the bis-indolyl impurity can be reduced to ≤5% area. In contrast, at 40° C. a side reaction is observed which lowers the yield of the compound of general formula (I).

Suitably therefore, after the addition of the compounds of general formulae (II) and (III), the reaction mixture is maintained at 15-25° C., suitably at room temperature, for example 18-22° C. and typically about 20° C., preferably with stirring, for about 10 to 24 hours, more usually 12 to 18 hours, for example about 15 hours.

In the process described above, values for amounts of various compounds are expressed in terms of % area. This refers to the percentage of the area of the peak representing a particular molecule on an HPLC trace.

The reduction step (ii) of the process may be carried out using any reducing agent capable of reducing a benzylic alcohol to the corresponding alkane, although triethylsilane has been found to be particularly suitable. Other silane reducing agents could also be used, however or alternatively another reduction method, for example hydrogenation, typically using a metal catalyst such as palladium or platinum. In this method, the reduction may be carried out under an inert atmosphere such as nitrogen or argon.

Conveniently, when triethylsilane is used as the reducing agent in step (ii), it is added slowly to the mixture obtained from step (i) over a period of about 1 to 3 hours, typically about 2 hours. The molar ratio of reducing agent to compound of general formula (II) is from about 2:1 to 4:1, for example about 3:1.

Reduction with triethyl silane requires acid conditions and this is provided by the titanium tetrachloride which remains in the reaction mixture after step (i). A further advantage of using $TiCl_4$ as the Lewis acid is that during the reduction step (ii), bis-indolyl impurity remaining in the reaction mixture slowly reverts to the intermediate of general formula (IVb) which is, in turn, reduced to give the compound of formula (I).

Once the reaction of step (ii) has proceeded to completion, the product of general formula (I) may be isolated. Therefore the process of the invention may additionally include the step of:
(iii) isolating and purifying the compound of general formula (I).

Suitably once the reduction has proceeded to completion, the temperature of the reaction mixture is reduced to about 0-5° C., following which water is added to the reaction mixture. The product may then be extracted into an organic solvent which may subsequently be removed by any appropriate means, for example distillation.

As set out above, the compound of formula (I) is an intermediate in the production of indole acetic acid derivatives which have pharmacological activity as CRTH2 antagonists and therefore in a further aspect the process of the invention includes the additional step of:

(iv) converting the compound of formula (I) to a compound of general formula (V):

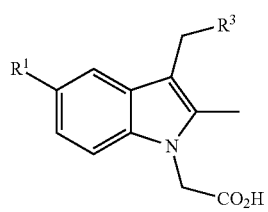

wherein $R^1$ and $R^3$ are as defined in general formula (I); the process comprising hydrolysing the compound of formula (I).

Either acid or base hydrolysis of the compound of formula (I) may be used, although base hydrolysis is particularly suitable.

Typically, hydrolysis will be conducted in aqueous solution using a strong base such as sodium, potassium or ammonium hydroxide. Potassium hydroxide is, however, particularly suitable. Suitably the base will be a 50% aqueous potassium hydroxide solution.

The amount of base used is typically 1.5 to 4 molar equivalents of the compound of formula (I). Suitably, the molar ratio of base:compound of formula (I) is about 2:1.

Step (v) may be carried out at room temperature, for example 20 to 25° C.

It has been found that, following the improvements to Stage 2 accorded by the process of the invention, the product of step (v) can be obtained in a form which is sufficiently pure for use as a pharmaceutical, so that further purification is unnecessary.

In order to obtain the starting material of general formula (II), the process may include additional steps before step (i).

Therefore, in a further aspect, the invention includes, before step (i), a process for the preparation of a compound of formula (II) comprising:

Reacting 5-fluoro-2-methyl indole with a compound of the formula (VI):

X—CH$_2$—COOR$^1$ (VI)

where X is a leaving group, for example a halo group such as bromo and $R^1$ is as defined for formula (I).

The reaction may take place in the presence of a weak base such as potassium or caesium carbonate, more usually caesium carbonate, in a polar organic solvent such as acetonitrile.

Suitably the amount of solvent used is from 7 to 30 L of solvent per kg of 5-fluoro-2-methyl indole, more usually from 7 to 20 L, for example about 7 to 15 L and suitably about 10 L of solvent per kg of 5-fluoro-2-methyl indole.

The reaction may be conducted at a temperature of from about 15 to 30° C., more usually 20-25° C. over a time of 10 to 36 hours, typically 18 to 30 hours, for example about 24 hours and the progress of the reaction may be monitored, for example by a chromatography method such as gas chromatography (GC).

When the reaction is complete, the compound of formula (II) may be isolated and/or purified in order to remove impurities such as 5-fluoro-2-methyl indole and compound of formula (VI). Alternatively, the purification step (iii) may be sufficient.

The presence of inorganic salts derived from the starting material of general formula (IV) is undesirable. Inorganic salts may be removed by washing the reaction mixture with water while maintaining the product of formula (II) in the organic phase. When a solvent such as acetonitrile is used as the reaction solvent, it may be advantageous to replace it at this stage with an alternative, less polar, solvent such as toluene.

The invention will now be described in greater detail with reference to the examples.

In the examples, the following abbreviations are used:

| | |
|---|---|
| TFA | Trifluoroacetic acid |
| TES | Triethyl silane |
| Et | Ethyl |
| DCM | dichloromethane |
| IPC | In process control |
| TMSOTf | Trimethylsilyl trifluoromethane sulfonate |
| TLC | Thin layer chromatography |
| HPLC | High performance liquid chromatography |

In the examples set out below, and in the whole specification values for amounts of various compounds are expressed in terms of % area. This refers to the percentage of the area of the peak representing a particular molecule on an HPLC trace. Suitable HPLC methods may be developed by those of skill in the art.

The HPLC parameters used in Comparative Example 4 and Example 5 are summarised in the table below.

| HPLC Parameter | Condition/Details | Additional Information |
|---|---|---|
| Detection Type/Wavelength | UV@ 220 HM | N/A |
| Column | Waters Eclipse XDB-C18 | 150 mm × 4.6 mm id 5µ |
| Injection Volume | 5 µL | N/A |
| Flow Rate | 1.5 mL/min | N/A |
| Run Time | 15 minutes | N/A |
| Mobile Phase A | 100% water | N/A |
| Mobile Phase B | 0.1% Formic Acid | N/A |
| Mobile Phase C | 100% Acetonitrile | N/A |
| Gradient System | Starting Conditions | 50:5:45 % A:B:C |
| | Time | % A:B:C |
| | 5 | 50:5:45 |
| | 10 | 15:5:80 |
| | 12 | 15:5:80 |
| | 14 | 50:5:45 |
| Column Temperature | 35° C. | N/A |

EXAMPLE 1—PREPARATION OF 5-FLUORO-2-METHYL-INDOLE N-ETHYL ACETATE (PROCESS STAGE 1)

Experimental Protocol

Into a reaction mixture of 1.0 Kg of 5-fluoro-2-methyl-indole (1.0 eq., 6.70 mol) and 0.99 kg of caesium carbonate (3.02 mol-0.45 eq.) with 9 L acetonitrile is added at 20-25°

C. over ~12 h a solution of 1.34 kg ethylbromoacetate (8.04 mol-1.2 eq.) in 1 L acetonitrile. Two additional charges of 0.99 kg caesium carbonate each are added after 4 hours and after 8 hours of reaction (3.02 mol-0.45 eq.). A final charge of 0.33 kg caesium carbonate is added (1.01 mol-0.15 eq.) and 0.056 kg of ethyl bromoacetate (0.335 mol-0.15 eq.) are added after 18 hours. The reaction mixture is maintained under agitation at 20-25° C. until the reaction is complete. 5 L of water is added to dissolve the inorganic salts. The agitation is maintained at 20-25° C. until complete dissolution of the inorganic salts then the reaction mixture is allowed to separate. The organic phase is concentrated to approximately 3 L. Toluene (5 L) is added then the mixture is concentrated to approximately 3 L. Toluene (5 L) is added to the reaction mixture; which is then washed with water (3 L) to eliminate the residual salts and concentrated to approximately 3 L under vacuum.

Expected Yield: 90±5%.

Scaled Up Method

The above method has been carried out with a batch size of up to 234 kg of 5-fluoro-2-methyl indole.

The quantity of (5-fluoro-2-methylindol-1-yl)-acetic acid ethyl ester recovered was 337 kg, a yield of 91.3%; which compared well with the expected yield of 90±5%.

EXAMPLE 2—INVESTIGATION OF REACTION CONDITIONS FOR SYNTHESIS OF [5-FLUORO-3-({2-[(4-FLUOROBENZENE)SULFONYL]PYRIDIN-3-YL}METHYL)-2-METHYL-INDOL-1-YL]-ACETIC ACID ETHYL ESTER

The reaction between 2-(4-Fluorobenzenesulfonyl)-pyridine-3-carboxaldehyde and 5-fluoro-2-methyl-indole N-ethyl acetate proceeds in two steps according to the scheme set out below. 2-(4-Fluorobenzenesulfonyl)-pyridine-3-carboxaldehyde may be prepared as described in WO2009/090414.

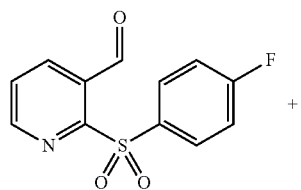

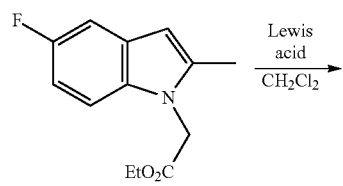

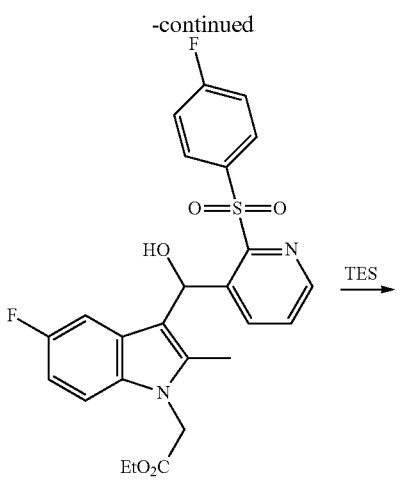

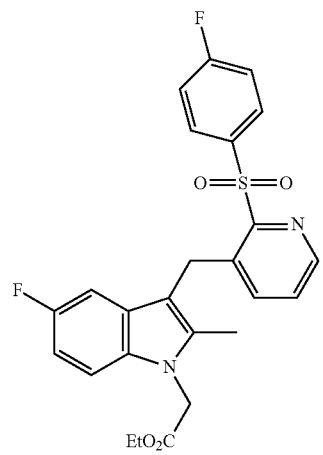

When conducted on a laboratory scale, the process described in WO2009/090414 leads to good quality material with acceptable yield but the very high dilution (50 vol of methylene chloride) and high cost of trimethylsilyl trifluoromethanesulfonate TMSOTf) as the Lewis acid were not considered acceptable for larger scale production.

Trials using TMSOTf were performed at higher concentration (about 10 volumes solvent per mass of starting indole) but in these experiments, the intermediate alcohol precipitated as a gummy material that agglomerated on the stirrer blade. This could lead to equipment damage at larger scale. At higher dilution (50 volumes solvent per mass of starting indole), the insoluble material was still present but did not agglomerate on the stirrer.

a) Step 1—Production of Intermediate Alcohol

A screen was performed in order to determine whether other Lewis acids could be used instead of TMSOTf. TFA, Trifluoromethanesulfonic acid (triflic acid), BF$_3$, AlCl$_3$, ZnBr$_2$ all led either to a high content of bis-indolyl impurity of the formula:

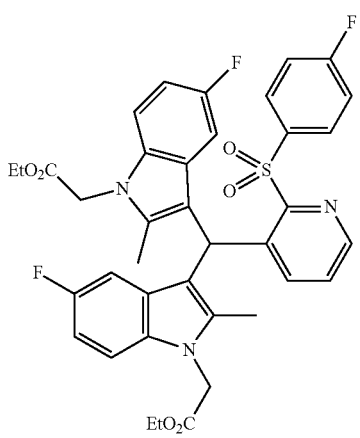 [SMILES: CCOC(=O)Cn1c(C)c(C(c2cccnc2S(=O)(=O)c2ccc(F)cc2)c2c(C)n(CC(=O)OCC)c3ccc(F)cc23)c2cc(F)ccc21]

or to an insoluble gummy material. With titanium chloride, however the alcohol intermediate precipitated as a brown solid leading to a stirrable suspension.

The results of six representative experiments are presented in Table 1 below which summarises the HPLC profile (area %) of the major components of the reaction mixtures before the reduction step. All of the reactions were carried out in 10-12 volumes of methylene chloride per mass of indole starting material.

The starting materials were introduced over 60-150 minutes at temperatures from −10 to +20° C. Several Lewis acids were tested and results are shown for $AlCl_3$, $ZnBr_2$ and $TiCl_4$.

The results of experiments (iii) (v) and (vi) show that varying the reaction temperature from −10° C. to 20° C. had no significant impact on the analytical profile of the reaction mixture.

In Exp. (iv), the stoichiometry of the titanium chloride was decreased from 2.0 to 1.1 and this led to the formation of a larger amount of bis-indolyl impurity (~20%).

b) Step 2—Reduction of Intermediate Alcohol to Give [5-Fluoro-3-({2-[(4-fluorobenzene)sulfonyl] pyridin-3-yl}methyl)-2-methylindol-1-yl]-acetic acid ethyl ester The reduction was performed with 3 equivalents of triethylsilane (TES) at room temperature.

Stability of the Intermediate Alcohol

The main impurity generated in the reaction is the bis-indolyl product resulting from the condensation of the intermediate with a second equivalent of indole starting material.

It is believed that, when a protic acid is used, the reaction proceeds as shown in Scheme 3 above, where the bis-indolyl impurity is in equilibrium with the alcohol. With some Lewis acids, particularly TMSOTf, the bis-indolyl impurity can be completely removed during the reduction step by the addition of water, which brings about reversion to the alcohol and indole starting material. However, this leads to a yield loss.

When the reaction was conducted using $TiCl_4$ as the Lewis acid, it was surprisingly found that under certain conditions the bis-indolyl product could be converted to the

TABLE 1

| Expt. | Addition time[1] | Lewis Acid/eq | Bis-indolyl (RRT 1.18) | Alcohol[2] (RRT 0.75 + 0.95) | Starting indole (RRT 0.78) | Extent of reaction when sample taken |
|---|---|---|---|---|---|---|
| (i) | 60 min/ 0° C. | $AlCl_3$ 2 eq | 55.1 | 28.2 | ND | End of addition of starting materials |
| (ii) | 60 min/ 0° C. | $ZnBr_2$ 2 eq | 30.8 | 46.6 | 19.5 | End of addition of starting materials |
| (iii) | 120 min/ −10° C. | $TiCl_4$ 2 eq | 10.8 | 85.8 | 0.1 | a) Approximately halfway through addition of starting materials |
|  |  |  | 9.6 | 83.3 | 0 | b) End of addition of starting materials |
| (iv) | 90 min/ 0° C. | $TiCl_4$ 1.1 eq | 9.9 | 86.6 | ND | a) Approximately halfway through addition of starting materials |
|  |  |  | 18.2 | 72.8 | 0 | b) End of addition of starting materials + 105 min aging at 20° C. |
| (v) | 120 min/ 0° C. | TiCl4 2 eq | 8.36 | 88.59 | ND | End of addition of starting materials |
| (vi) | 120 min/ 20° C. | $TiCl_4$ 2 eq | 10.4 | 86.2 | ND | a) End of addition of starting materials |
|  |  |  | 4.6 | 89.8 | 0.1 | b) 20 h after the addition of starting materials |

[1]i.e. time taken to add starting materials and reaction temperature upon dosing of a solution of the aldehyde and the indole onto the Lewis acid
[2]the HPLC chromatograms show two peaks that disappeared during the reduction step. The major one was identified as the alcohol by LC/MS. The value in the table is the sum of the area % of the two peaks.

When the results for experiments (i) and (ii) are compared with those for experiments (iii) to (vi) it can be seen that the amount of bis-indolyl impurity was significantly higher and the amount of alcohol was significantly lower using $AlCl_3$ or $ZnBr_2$ as the Lewis acid than when $TiCl_4$ was used.

required product. This led the inventors to speculate that the reaction may proceed via one or more alternative intermediates instead of, or in addition to the alcohol. However, the nature of these intermediates has not been investigated at this time.

Thus, during a stability study of the reaction mixture (Experiment vi) it was demonstrated that at 20° C. the reverse reaction leading from the bis-indolyl to an intermediate is favoured; leading after 24 h of stirring to a level of bis-indolyl by-product lower than 5%. At 40° C., a degradation of the alcohol is observed.

Results from the whole reaction, including the reduction step are shown below in Table 2. Results are provided for the reduction stage of the experiments (iii), (v) and (vi) shown in Table 1 above; together with additional experiments carried out using TMSOTf as the Lewis acid. All reactions were performed in 10-12 volumes of methylene chloride per mass of indole starting material apart from Experiment (ix), which was performed in 50 volumes. With the titanium chloride process, the viscosity of the reaction mixture increases during the reduction and it is therefore necessary to add the TES slowly to the reaction mixture.

Our results show that using $TiCl_4$ or TMSOTf as a Lewis acid did not lead to a significant difference in the content of the bis-indolyl at the end of the reduction step.

When TMSOTf is used, the addition of a small amount of water leads to the disappearance of the bis-indolyl impurity over a period of 1-3 hours and to the formation of the indole starting material and the required product. Thus, although the bis-indolyl impurity can be removed without difficulty, Table 2 shows that a decrease in yield of the required product and, an increase in the amount of starting indole is observed for Experiments (vii), (viii) and (ix) when compared to Experiments (iii), (v) and (vi).

With titanium chloride as Lewis acid, the bis-indolyl slowly reverts to an intermediate, which is then reduced to the required product.

The HPLC profile of the reaction mixture after reduction is similar or better if using titanium chloride instead of TMSOTf.

EXAMPLE 3—PREPARATION OF [5-FLUORO-3-({2-[(4-FLUOROBENZENE)SULFONYL]PYRIDIN-3-YL}METHYL)-2-METHYLINDOL-1-YL]-ACETIC ACID ETHYL ESTER

Experimental Protocol

A reactor is charged with 1.612 kg of $TiCl_4$ (2 equivalents with respect to 5-fluoro-2-methyl-indole N-ethyl acetate) and 5 liters of dichloromethane. The vessel is cooled to 0±3° C. A solution of 1 kg 5-fluoro-2-methyl-indole N-ethyl acetate and 1.18 kg of 2-(4-fluorobenzenesulfonyl)-pyridine-3-carboxaldehyde (1.05 equiv.) in 6 liters of dichloromethane is prepared using another vessel and is added to the $TiCl_4$ solution over a period of 2 hours, keeping the temperature at 0±3° C. (the formation of a precipitate is observed during the addition). The vessel is rinsed with 1 liter of dichloromethane, which is then added to the reaction mixture. The mixture is heated up to 20±3° C. and held at this temperature for 15 hours until completion of the reaction.

1.483 kg of triethylsilane (3 equiv) is added to the mixture, at 20±3° C., over about 2 hours. The charging vessel and lines are rinsed with 0.5 liter of dichloromethane, which is added to the reaction and the slurry is maintained at 20±3° C. for 4 hours until judged complete by HPLC.

Work-Up

The slurry is cooled to 0-5° C. and 4 liters of water is added quickly, keeping the temperature below 20° C. The aqueous layer is separated and washed with 2 liters of dichloromethane. The organic layers are combined and washed with 3 liters of water, followed by an aqueous solution of sodium bicarbonate (9% w/w), until pH of the aqueous phase reaches 8.0±1. The aqueous layer is discarded and the organic phase is further washed with 2 liters

TABLE 2

| Expt | Addition on time[1] | Lewis Acid/eq | TES[2] Charging time/Temp | Bis-indolyl RRT 1.18 | Alcohol RRT 0.75 + 0.95 | Prod | Starting material RRT 0.78 | When measured |
|---|---|---|---|---|---|---|---|---|
| (iii) | 120 min/ −10° C. | $TiCl_4$ 2 eq | 20 min/ 0° C. | 10.8 | 85.8 | ND | 0.1 | a) Approximately half way through addition |
|  |  |  |  | 9.6 | 83.3 | 4.8 | 0 | b) End of addition |
|  |  |  |  | ND | ND | 92.1 | 4.8 | c) after overnight stirring with TES |
| (v) | 120 min/ 0° C. | $TiCl_4$ 2 eq | 110 min 20° C. | 8.36 | 88.59 | 1.05 | ND | a) End addition of starting materials |
|  |  |  |  | 2.74 | 93.29 | 2.109 | ND | b) Before TES charge = 23 H at 20° C. |
|  |  |  |  | ND | ND | 94.0 | 1.17 | c) TES 18 H |
| (vi) | 120 min/ 20° C. | $TiCl_4$ 2 eq | 80 min/ 20° C. | 10.4 | 86.2 | 1.2 | ND | a) End addition of starting materials |
|  |  |  |  | 4.6 | 89.8 | 2.9 | 0.1 | b) Before TES charge = 21 H 15 at 20° C. |
|  |  |  |  | 0.9 | 1.1 | 94.8 | 1.2 | c) TES 4 h 15 |
| (vii) | 120 min/ 0° C. | TMS-OTf 2 eq | 2 min/ 0° C. | 13.1 | ND | 77.6 | 1.5 | a) 1 h after TES addition |
|  |  |  |  | 5.2 | ND | 83.5 | 4.8 | b) 20 h after TES addition |
| (viii) | 100 min/ 0° C. | TMS-OTf 2 eq | 2 min/ 0° C. | 11.2 | ND | 76.6 | 1.3 | a) 2 h 45 after TES charge |
|  |  |  |  | 1.7 |  | 83.8 | 5.7 | b) After 1.0 eq water |
| (ix) | 120 min/ 0° C. | TMS-OTf 2 eq | 2 min/ 0° C. | 11.5 | ND | 83 | 1.5 | a) 1 h after TES charge |
|  |  |  |  | 0.1 | ND | 89.5 | 5.2 | b) After 1.0 eq water |

[1] i.e. time taken to add starting materials and reaction mixture temperature of the dosing of a solution of the aldehyde and the indole onto the Lewis acid
[2] TES dosing time and reaction mixture temperature of water and the pH is checked (pH=8.0±1). The objective at this point is to neutralise the HCl from the hydrolysis of titanium tetrachloride.

The organic layer is dried by azeotropic distillation under atmospheric pressure. The dried solution is filtered into another vessel and the filtrate is concentrated to a residual volume of about 6 liters (6 vol). Ethanol (6 liters) is then added keeping the temperature above 50° C. and the mixture is concentrated to a residual volume of about 6 liters. The product crystallizes during concentration. A further 2 liters of ethanol are added and the suspension is concentrated again to 6 liters. At the end of this step the temperature at the top of the distillation column is above 76° C.

The suspension is cooled to 20±3° C. and filtered. The wet cake is washed twice with 3 liters of ethanol at 20±3° C., air dried and transferred to a vacuum dryer. The product is dried at 55° C. under vacuum.

Yield=85±7%.

Scaled Up Method

The reaction described above was carried out using 8 kg 5-fluoro-2-methyl-indole N-ethyl acetate and 9.5 kg of 2-(4-fluorobenzenesulfonyl)-pyridine-3-carboxaldehyde in 48 L dichloromethane which was added to 12.9 kg of titanium tetrachloride in 40 L dichloromethane. During introduction of the starting materials, the intermediate alcohol precipitated but the mixture did not become too thick and stirring remained efficient. The amount of triethylsilane used for the reduction was 12 kg. The amount of [5-fluoro-3-({2-[(4-fluorobenzene)sulfonyl]pyridin-3-yl}methyl)-2-methylindol-1-yl]-acetic acid ethyl ester obtained was 13.8 kg, an overall yield of 84.2%. The purity of the product was 99% area by HPLC or 96.1% w/w.

A further pilot run was carried out using 7.7 kg 5-fluoro-2-methyl-indole N-ethyl acetate and 9.1 kg of 2-(4-fluorobenzenesulfonyl)-pyridine-3-carboxaldehyde in 46 L dichloromethane which was added to 12.4 kg of titanium tetrachloride in 39 L dichloromethane. The amount of triethylsilane used in the reduction step was 11.4 kg.

13.5 kg (85.6% yield) of product was obtained and analysis showed that the purity of the product was 99% area by HPLC or 98.2% w/w.

The process of the invention was therefore demonstrated to give a product with a yield which was consistently greater than 80% and of which the purity was consistently greater than 95% w/w.

The product obtained may be converted to [5-Fluoro-3-({2-[(4-fluorobenzene)sulfonyl]pyridin-3-yl}-2-m y ethyl-indol-1-yl]-acetic acid using the method set out in WO2009/090414.

COMPARATIVE EXAMPLE 4—SYNTHESIS OF (3-{[2-(BENZENESULFONYL)PYRIDIN-3-YL]METHYL}-5-FLUORO-2-METHYLINDOL-1-YL)-ACETIC ACID ETHYL ESTER USING TMSOTF

Using a similar method to that set out in WO2009/090414, an experiment was conducted using TMSOTf as the Lewis acid for the coupling of 5-fluoro-2-methyl-indole N-ethyl acetate and 2-(benzenesulfonyl)-pyridine-3-carboxaldehyde, followed by reduction with TES. 2-(Benzenesulfonyl)-pyridine-3-carboxaldehyde was prepared according to the method similar to that set out in WO2009/090414.

A solution of TMSOTf (31.0 g, 0.139 mol) in dichloromethane (310 mL) was cooled to −5° C. under a nitrogen atmosphere. A solution of 5-fluoro-2-methyl-indole N-ethyl acetate (10.92 g, 0.046 mol) and 2-(benzenesulfonyl)-pyridine-3-carboxaldehyde (11.46 g, 0.046 mol) in dichloromethane (310 mL) was added to the triflate solution over 40 min maintaining the temperature at 0° C. The reaction mixture was aged for a further 30 min, then triethylsilane (16.2 g, 0.140 mol) was added and warmed to ambient temperature. Sodium bicarbonate solution (saturated, 225 mL) was added, the phases separated and the organic phase was washed with water (100 ml) then concentrated to dryness. Some supernatant liquid was removed from the oil by decantation and the residual oil was triturated with water (140 mL) to produce a solid. The solid was dissolved in acetone (90 mL) at 50° C. and crystallized by the addition of water (35 mL) at 0° C. The product was filtered and dried in a vacuum oven overnight to yield the desired product (14.7 g, 68%). LC-MS analysis showed the product to be a single component.

Because of the high dilution necessary and the low yield obtained using this method, an alternative synthesis was attempted using titanium tetrachloride as the Lewis acid rather than TMSOTf.

EXAMPLE 5—SYNTHESIS OF (3-{[2-(BENZENESULFONYL)PYRIDIN-3-YL]METHYL}-5-FLUORO-2-METHYLINDOL-1-YL)-ACETIC ACID ETHYL ESTER USING TITANIUM TETRACHLORIDE AS THE LEWIS ACID

The method of Example 3 was repeated using 2-(benzenesulfonyl)-pyridine-3-carboxaldehyde as a starting material in place of 2-(4-fluorobenzenesulfonyl)-pyridine-3-carboxaldehyde. This may be prepared by the method set out in WO2009/090414. The reaction was first conducted on an 11 g scale of 2-(benzenesulfonyl)-pyridine-3-carboxaldehyde and was subsequently repeated on a 150 g and a 230 g scale. The method for the 150 g scale experiment is as follows.

Titanium tetrachloride (219.2 g, 1.155 mol, Aldrich 99.9%) was dissolved in DCM (0.54 L) and cooled to −5° C. A solution of 2-(benzenesulfonyl)-pyridine-3-carboxaldehyde (150.0 g, 0.607 mol) and 5-fluoro-2-methyl-indole N-ethyl acetate (135.9 g, 0.578 mol) in dichloromethane (0.81 L) was added over 2 hours 10 minutes maintaining the temperature below 00° C. (typically −1° C.). The reaction was aged for a further 2 hours with the mixture developing into a thick slurry. TLS (ethyl acetate/heptane 1:1) and LC-MS indicated complete consumption of starting materials. Triethylsilane (201.5 g, 1.737 mol, Aldrich 99%) was added over 2 hours, maintaining the temperature at 20-25° C., then stirred at 20-25° C. overnight. A darkening of the reaction mixture was observed during the addition of the reducing agent. The reaction mixture was cooled to 0-5° C. and water (0.54 L) was added maintaining the exotherm at <15° C. The solids dissolved during the water addition and the resulting aqueous and organic phases were separated. The organic phase was sequentially washed with water (0.70 L), sodium bicarbonate (saturated 2×0.50 L) and water (0.50 L). The organic product solution was concentrated to half volume and ethanol (1.30 L) was added resulting in crystallization of the product. The volume of the slurry was again concentrated to half volume and then diluted with additional ethanol (0.75 L). The slurry was stirred for 1 hour at 20-25° C., filtered and the cake washed with ethanol (0.30 L), then dried under vacuum at <40° C. to give the product as a white solid (213.5 g, 79% yield). HPLC analysis showed 99.6% area of the required product with three impurities at relative retention times of 0.15 (0.06%), 0.87 (0.08%) and 1.07 (0.25%).

The method of the present invention represents a significant improvement over methods described in earlier documents as it is generally applicable to many different indole acetic acid derivatives, which methods using TFA are not. Furthermore, the reaction may be carried out using a greatly reduced amount of solvent compared with methods employing TMSOTf as the Lewis acid and it is also higher yielding.

The invention claimed is:

1. A process for the preparation of a compound of general formula (I):

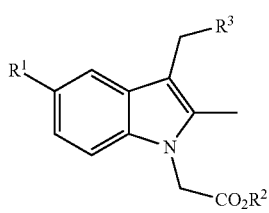

wherein $R^1$ is fluoro, chloro or bromo;
$R^2$ is $C_1$-$C_6$ alkyl or benzyl; and
$R^3$ is aryl or heteroaryl optionally substituted with one or more substituents selected from halo, OH, CN, $R^4$, COR$^4$, CH$_2$R$^4$, OR$^4$, SR$^4$, SO$_2$R$^4$, or SO$_2$YR$^4$;
$R^4$ is $C_1$-$C_6$ alkyl, $C_3$-$C_8$ cycloalkyl, heterocyclyl, aryl, or heteroaryl, any of which may optionally be substituted with one or more substituents selected from halo, OH, CN, NO$_2$, $C_1$-$C_6$ alkyl, or O($C_1$-$C_6$ alkyl); and
Y is NH or a straight or branched $C_1$-$C_4$ alkylene chain;
the process comprising:
  i. reacting a compound of general formula (II):

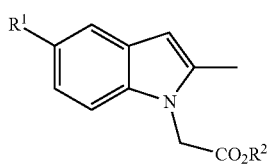

wherein $R^1$ and $R^2$ are as defined for general formula (I);
with a compound of general formula (III)

wherein $R^3$ is as defined for general formula (I);
in a suitable solvent and in the presence of titanium tetrachloride, wherein the ratio of the compound of general formula (II) to solvent is from 1:8 to 1:20 weight/volume; and
  ii. reacting the product of (i) with a reducing agent to give a compound of general formula (I).

2. The process of claim 1, wherein, in the compound of general formula (I), independently or in any combination:
$R^1$ is fluoro;
$R^2$ is $C_1$-$C_4$ alkyl; and
$R^3$ is quinoline, quinoxaline, isoquinoline, thiazole, phenyl, naphthalene, thiophene, pyrrole, or pyridine, any of which may optionally be substituted as set out in claim 1.

3. The process of claim 1, in the compound of general formula (I), $R^2$ is methyl or ethyl.

4. The process of claim 1 wherein, in the compound of general formula (I), $R^3$ is quinoline, isoquinoline, phenyl, naphthalene, thiophene, pyrrole, or pyridine, any of which may optionally be substituted as set out in claim 1.

5. The process of claim 4 wherein, in the compound of general formula (I), $R^3$ is quinoline or isoquinoline, either of which is unsubstituted or substituted with one or more halo substituents.

6. The process of claim 1 wherein, in the compound of general formula (I), $R^3$ is phenyl, naphthalene, thiophene, pyrrole, or pyridine, any of which is optionally substituted with one or more substituents, selected from OR$^4$, SO$_2$R$^4$, or SO$_2$YR$^4$; where $R^4$ and Y are as defined in claim 1.

7. The process of claim 1 for the preparation of a compound of formula (Ia):

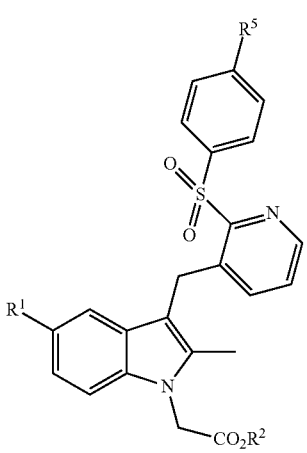

wherein $R^1$ and $R^2$ are as defined in claim 1; and
$R^5$ is hydrogen, halo, —CN, —$C_1$-$C_6$ alkyl, —SOR$^7$, —SO$_2$R$^7$, —SO$_2$N(R$^6$)$_2$, —N(R$^6$)$_2$, —NR$^6$C(O)R$^7$, —CO$_2$R$^6$, —CONR$^6$R$^7$, —NO$_2$, —OR$^6$, —SR$^6$, —O(CH$_2$)$_p$OR$^6$, or —O(CH$_2$)$_p$O(CH$_2$)$_q$OR$^6$, wherein
each R$^6$ is independently hydrogen, —C$_1$-C$_6$ alkyl, —C$_3$-C$_8$ cycloalkyl, aryl, or heteroaryl;
each R$^7$ is independently, —C$_1$-C$_6$ alkyl, —C$_3$-C$_8$ cycloalkyl, aryl, or heteroaryl; and
p and q are each independently an integer from 1 to 3.

8. The process of claim 7 wherein, in the compound of general formula (Ia), independently or in combination:
$R^1$ is fluoro;
$R^2$ is methyl or ethyl; and
$R^5$ is hydrogen, fluoro, or chloro.

9. The process of claim 1 for the preparation of a $C_1$-$C_6$ alkyl or benzyl ester of:
(5-Fluoro-2-methyl-3-quinolin-2-ylmethyl-indol-1-yl)-acetic acid;
(5-Fluoro-2-methyl-3-naphthalen-2-ylmethyl-indol-1-yl)-acetic acid;
[5-Fluoro-3-(8-hydroxyquinolin-2-ylmethyl)-2-methyl-indol-1-yl]-acetic acid;
[5-Fluoro-2-methyl-3-(quinoxalin-2-ylmethyl)indol-1-yl]-acetic acid;

[5-Fluoro-3-(4-methoxy-benzyl)-2-methyl-indol-1-yl]-acetic acid;

[5-Fluoro-2-methyl-3-(1,3-thiazol-2-ylmethyl)indol-1-yl]-acetic acid;

[3-(4-Chloro-benzyl)-5-fluoro-2-methyl-indol-1-yl]-acetic acid;

[5-Fluoro-2-methyl-3-(4-trifluoromethyl-benzyl)-indol-1-yl]-acetic acid;

[5-Fluoro-2-methyl-3-(4-tert-butyl-benzyl)-indol-1-yl]-acetic acid;

{5-Fluoro-2-methyl-3-[(4-phenylphenyl)methyl]indol-1-yl}-acetic acid;

[5-Fluoro-3-(4-methanesulfonyl-benzyl)-2-methyl-indol-1-yl]-acetic acid;

{5-Fluoro-3-[(6-fluoroquinolin-2-yl)methyl]-2-methylindol-1-yl}-acetic acid;

(5-Chloro-2-methyl-3-quinolin-2-ylmethyl-indol-1-yl)-acetic acid;

(3-{[1-(Benzenesulfonyl)pyrrol-2-yl]methyl}-5-fluoro-2-methylindol-1-yl)-acetic acid;

[5-Fluoro-2-methyl-3-({1-[(4-methylbenzene)sulfonyl]pyrrol-2-yl}methyl)indol-1-yl]-acetic acid;

[3-({1-[(2,4-Difluorobenzene)sulfonyl]pyrrol-2-yl}methyl)-5-fluoro-2-methylindol-1-yl]-acetic acid;

(3-{[2-(Benzenesulfonyl)phenyl]methyl}-5-fluoro-2-methylindol-1-yl)-acetic acid;

[3-({2-[(4-Chlorobenzene)sulfonyl]phenyl}methyl)-5-fluoro-2-methyindol-1-yl]-acetic acid;

[5-Fluoro-3-({2-[(4-fluorobenzene)sulfonyl]phenyl}methyl)-2-methylindol-1-yl]-acetic acid;

(3-{[2-(Benzenesulfonyl)pyridin-3-yl]methyl}-5-fluoro-2-methylindol-1-yl)-acetic acid;

[5-Fluoro-3-({2-[(4-fluorobenzene)sulfonyl]pyridin-3-yl}methyl)-2-methylindol-1-yl]-acetic acid;

[3-({2-[(4-Chlorobenzene)sulfonyl]pyridin-3-yl}methyl)-5-fluoro-2-methylindol-1-yl]-acetic acid;

2-(3-(2-(Cyclohexylsulfonyl)benzyl)-5-fluoro-2-methyl-indol-1-yl)-acetic acid;

2-(5-Fluoro-2-methyl-3-(2-(piperidin-1-ylsulfonyl)benzyl)-indol-1-yl)-acetic acid;

2-(3-(2-(Cyclopentylsulfonyl)benzyl)-5-fluoro-2-methyl-indol-1-yl)-acetic acid;

2-(5-Fluoro-2-methyl-3-(3-(piperidin-1-ylsulfonyl)benzyl)-indol-1-yl)-acetic acid;

2-(5-Fluoro-2-methyl-3-(2-(pyrrolidin-1-ylsulfonyl)benzyl)-indol-1-yl)-acetic acid;

2-(3-(4-(Cyclohexylsulfonyl)benzyl)-5-fluoro-2-methyl-indol-1-yl)-acetic acid;

2-(3-(4-(Cyclopentylsulfonyl)benzyl)-5-fluoro-2-methyl-indol-1-yl)-acetic acid;

2-(3-(2-(Cyclobutylsulfonyl)benzyl)-5-fluoro-2-methyl-indol-1-yl)-acetic acid;

2-(5-Fluoro-2-methyl-3-(3-(pyrrolidin-1-ylsulfonyl)benzyl)-indol-1-yl)-acetic acid;

2-(5-Fluoro-2-methyl-3-(4-(piperidin-1-ylsulfonyl)benzyl)-indol-1-yl)-acetic acid;

[5-Fluoro-2-methyl-3-(2-phenoxybenzyl)-indol-1-yl]-acetic acid;

[5-Fluoro-2-methyl-3-(2-(4-methoxyphenoxy)benzyl)-indol-1-yl]-acetic acid;

[5-Fluoro-2-methyl-3-(2-(4-methylphenoxy)benzyl)-indol-1-yl]-acetic acid;

[5-Fluoro-2-methyl-3-(2-(2,4-dichlorophenoxy)benzyl)-indol-1-yl]-acetic acid;

[5-Fluoro-2-methyl-3-(2-(4-fluorophenoxy)benzyl)-indol-1-yl]-acetic acid;

[5-Fluoro-2-methyl-3-(2-(3,4-difluorophenoxy)benzyl)-indol-1-yl]-acetic acid;

[5-Fluoro-2-methyl-3-(2-(4-cyanophenoxy)benzyl)-indol-1-yl]-acetic acid;

[5-Fluoro-2-methyl-3-(2-(4-chlorophenoxy)benzyl)-indol-1-yl]-acetic acid;

[5-Fluoro-2-methyl-3-(2-(2-cyanophenoxy)benzyl)-indol-1-yl]-acetic acid;

(5-Fluoro-2-methyl-3-{[2-(4-methylphenoxy)pyridin-3-yl]methyl}indol-1-yl)-acetic acid;

{5-Fluoro-3-[(3-methanesulfonylnaphthalen-2-yl)methyl]-2-methylindol-1-yl}-acetic acid;

{5-Fluoro-3-[(1-methanesulfonylnaphthalen-2-yl)methyl]-2-methylindol-1-yl}-acetic acid;

{5-Fluoro-3-[(6-methanesulfonylnaphthalen-2-yl)methyl]-2-methylindol-1-yl}-acetic acid;

[5-Fluoro-2-methyl-3-(quinolin-3-ylmethyl)indol-1-yl]-acetic acid;

[5-Fluoro-2-methyl-3-(quinoxalin-6-ylmethyl)indol-1-yl]-acetic acid;

[5-Fluoro-2-methyl-3-(quinolin-7-ylmethyl)indol-1-yl]-acetic acid;

{5-Fluoro-3-[(6-methanesulfonylquinolin-2-yl)methyl]-2-methylindol-1-yl}-acetic acid;

{5-Fluoro-3-[(4-methanesulfonylquinolin-2-yl)methyl]-2-methylindol-1-yl}-acetic acid;

(5-Fluoro-2-methyl-3-{pyrazolo[1,5-a]pyridin-3-ylmethyl}indol-1-yl)-acetic acid;

(5-Fluoro-3-{imidazo[1,2-a]pyridin-2-ylmethyl}-2-methylindol-1-yl)-acetic acid;

(5-Fluoro-2-methyl-3-{[2-(methylsulfanyl)phenyl]methyl}indol-1-yl)-acetic acid;

(5-Fluoro-2-methyl-3-{[3-(methylsulfanyl)phenyl]methyl}indol-1-yl)-acetic acid;

(5-Fluoro-2-methyl-3-{[4-(ethylsulfanyl)phenyl]methyl}indol-1-yl)-acetic acid(3-{[4-(Ethylsulfanyl)phenyl]methyl}-5-fluoro-2-methylindol-1-yl)-acetic acid;

(5-Fluoro-2-methyl-3-{[4-(n-propylsulfanyl)phenyl]methyl}indol-1-yl)-acetic acid;

(5-Fluoro-2-methyl-3-{[4-(i-propylsulfanyl)phenyl]methyl}indol-1-yl)-acetic acid;

(5-Fluoro-2-methyl-3-{[4-(t-butylsulfanyl)phenyl]methyl}indol-1-yl)-acetic acid;

(5-Fluoro-2-methyl-3-{[4-(pentan-3-ylsulfanyl)phenyl]methyl}indol-1-yl)-acetic acid;

[3-({4-[(Cyclopropylmethyl)sulfanyl]phenyl}methyl)-5-fluoro-2-methylindol-1-yl]-acetic acid;

{3-[(4,4-Dimethyl-2,3-dihydro-1-benzothiopyran-6-yl)methyl]-5-fluoro-2-methylindol-1-yl}-acetic acid;

(3-{[2-(Ethanesulfonyl)phenyl]methyl}-5-fluoro-2-methylindol-1-yl)-acetic acid;

(5-Fluoro-2-methyl-3-{[2-(propane-1-sulfonyl)phenyl]methyl}indol-1-yl)-acetic acid;

(5-Fluoro-2-methyl-3-{[2-(propane-2-sulfonyl)phenyl]methyl}indol-1-yl)-acetic acid;

(3-{[2-(Butane-1-sulfonyl)phenyl]methyl}-5-fluoro-2-methylindol-1-yl)-acetic acid;

(3-{[2-(Butane-2-sulfonyl)phenyl]methyl}-5-fluoro-2-methylindol-1-yl)-acetic acid;

(5-Fluoro-2-methyl-3-{[2-(2-methylpropane-2-sulfonyl)phenyl]methyl}indol-1-yl)-acetic acid;

(5-Fluoro-2-methyl-3-{[2-(pentane-1-sulfonyl)phenyl]methyl}indol-1-yl)-acetic acid;

(3-{[2-(Cyclopropylmethane)sulfonylphenyl]methyl}-5-fluoro-2-methylindol-1-yl)-acetic acid;

(5-Fluoro-2-methyl-3-{[2-(propylsulfamoyl)phenyl]
methyl}indol-1-yl)-acetic acid;
(3-{[2-(Butylsulfamoyl)phenyl]methyl}-5-fluoro-2-
methylindol-1-yl)-acetic acid;
(5-Fluoro-2-methyl-3-{[3-(propylsulfamoyl)phenyl]
methyl}indol-1-yl)-acetic acid;
(3-{[3-(Butylsulfamoyl)phenyl]methyl}-5-fluoro-2-
methylindol-1-yl)-acetic acid;
(5-Fluoro-2-methyl-3-{[4-(trifluoromethane)sulfonyl-
phenyl]methyl}indol-1-yl)-acetic acid;
(3-{[4-(Ethanesulfonyl)phenyl]methyl}-5-fluoro-2-meth-
ylindol-1-yl)-acetic acid;
(5-Fluoro-2-methyl-3-{[4-(propane-1-sulfonyl)phenyl]
methyl}indol-1-yl)-acetic acid;
(5-Fluoro-2-methyl-3-{[4-(propane-2-sulfonyl)phenyl]
methyl}indol-1-yl)-acetic acid;
(3-{[4-(Butane-1-sulfonyl)phenyl]methyl}-5-fluoro-2-
methylindol-1-yl)-acetic acid;
(5-Fluoro-2-methyl-3-{[4-(2-methylpropane-2-sulfonyl)
phenyl]methyl}indol-1-yl)-acetic acid;
(5-Fluoro-2-methyl-3-{[4-(pentane-1-sulfonyl)phenyl]
methyl}indol-1-yl)-acetic acid;
(5-Fluoro-2-methyl-3-{[4-(pentan-3-ylsulfonyl)phenyl]
methyl}indol-1-yl)-acetic acid;
[3-({4-[(Cyclopropylmethyl)sulfonyl]phenyl}methyl)-5-
fluoro-2-methylindol-1-yl]-acetic acid;
(5-Fluoro-2-methyl-3-{[4-(propylsulfamoyl)phenyl]
methyl}indol-1-yl)-acetic acid;
(3-{[4-(Butylsulfamoyl)phenyl]methyl}-5-fluoro-2-
methylindol-1-yl)-acetic acid;
(5-Fluoro-2-methyl-3-{[4-(trifluoromethoxy)phenyl]
methyl}indol-1-yl)-acetic acid;
(5-Fluoro-3-{[4-methanesulfonyl-3-(trifluoromethyl)
phenyl]methyl}-2-methylindol-1-yl)-acetic acid;
(5-Fluoro-3-{[4-methanesulfonyl-3-(trifluoromethoxy)
phenyl]methyl}-2-methylindol-1-yl)-acetic acid;
{5-Fluoro-3-[(5-methanesulfonylthiophen-2-yl)methyl]-
2-methylindol-1-yl}-acetic acid;
{3-[(4,4-dimethyl-1,1-dioxo-2,3-dihydro-1$\lambda^6$-benzothio-
pyran-6-yl)methyl]-5-fluoro-2-methylindol-1-yl}-ace-
tic acid;
[3-({1-[(4-Chlorobenzene)sulfonyl]pyrrol-2-yl}methyl)-
5-fluoro-2-methylindol-1yl]-acetic acid;
[5-Fluoro-3-({1-[(4-fluorobenzene)sulfonyl]pyrrol-2-
yl}methyl)-2-methylindol-1-yl]-acetic acid;
[5-Fluoro-3-({1-[(4-methoxybenzene)sulfonyl]pyrrol-2-
yl}methyl)-2-methylindol-1-yl]-acetic acid;
{3-[1-(2,4-Dichloro-benzenesulfonyl)pyrrol-2-ylmethyl]-
5-fluoro-2-methyl-indol-1-yl}-acetic acid;
{5-Fluoro-2-methyl-3-[(2-phenylphenyl)methyl]indol-1-
yl}-acetic acid;
(3-{[1-(Benzenesulfonyl)indol-2-yl]methyl}-5-fluoro-2-
methylindol-1-yl)-acetic acid;
(3-{[2-(4-Chlorophenyl)phenyl]methyl}-5-fluoro-2-
methylindol-1-yl)-acetic acid;
(5-Fluoro-2-methyl-3-{[2-(4-methylphenyl)phenyl]
methyl}indol-1-yl)-acetic acid;
{5-Fluoro-2-methyl-3-[(3-phenoxyphenyl)methyl]indol-
1-yl}-acetic acid;
[5-Fluoro-3-({4-[(4-fluorophenyl)carbonyl]-1-methyl-
pyrrol-2-yl}methyl)-2-methylindol-1-yl]-acetic acid;
{5-Fluoro-2-methyl-3-[(6-{[3-(trifluoromethyl)phenyl]
methyl}pyridin-3-yl)methyl]indol-1-yl}-acetic acid;
{5-Fluoro-2-methyl-3-[(3-phenoxythiophen-2-yl)methyl]
indol-1-yl}-acetic acid;
(3-{[2-(Benzenesulfonyl)-1,3-thiazol-5-yl]methyl}-5-
fluoro-2-methylindol-1-yl)-acetic acid;
{3-[(1-Benzylpyrazol-4-yl)methyl]-5-fluoro-2-methylin-
dol-1-yl}-acetic acid;
(3-{[5-(4-Chlorophenoxy)-1-methyl-3-(trifluoromethyl)
pyrazol-4-yl]methyl}-5-fluoro-2-methylindol-1-yl)-
acetic acid;
[3-({5-[(4-Chlorobenzene)sulfonyl]furan-2-yl}methyl)-
5-fluoro-2-methylindol-1-yl]-acetic acid;
[3-({5-[(4-Chlorobenzene)sulfonyl]thiophen-2-
yl}methyl)-5-fluoro-2-methylindol-1yl]-acetic acid;
[3-({3-[(4-Chlorobenzene)sulfonyl]thiophen-2-
yl}methyl)-5-fluoro-2-methylindol-1-yl]-acetic acid;
or
{3-[(2-Benzylphenyl)methyl]-5-fluoro-2-methylindol-1-
yl}-acetic acid.

10. The process of claim 1 for the preparation of a $C_1$-$C_6$ alkyl or benzyl ester of:
(3-{[2-(Benzenesulfonyl)pyridin-3-yl]methyl}-5-fluoro-
2-methylindol-1-yl)-acetic acid;
[5-Fluoro-3-({2-[(4-fluorobenzene)sulfonyl]pyridin-3-
yl}methyl)-2-methylindol-1-yl]-acetic acid; or
[3-({2-[(4-Chlorobenzene)sulfonyl]pyridin-3-
yl}methyl)-5-fluoro-2-methylindol-1-yl]-acetic acid.

11. The process of claim 1, wherein the solvent is a halogenated solvent.

12. The process of claim 11, wherein the solvent is dichloromethane.

13. The process of claim 1, wherein the ratio of the compound of general formula (II) to solvent is from 1:10 to 1:12 weight/volume.

14. The process of claim 1, wherein the molar ratio of titanium tetrachloride to the compound of formula (II) is from 1:1 to 3:1.

15. The process of claim 14, wherein the molar ratio of titanium tetrachloride to the compound of formula (II) is from about 1.8:1 to 2.2:1.

16. The process of claim 1, wherein the reaction temperature of (i) is −10 to 25° C.

17. The process of claim 1, wherein, in (i) after the addition of the compounds of general formulae (II) and (III), the reaction mixture is stirred for about 12 to 18 hours.

18. The process of claim 1, wherein, in (ii), the reduction is carried out using triethylsilane.

19. The process of claim 18, wherein the molar ratio of triethylsilane to the compound of general formula (II) is from about 2:1 to 4:1.

20. The process of claim 1, further comprising:
(iii) isolating and purifying the compound of general formula (I).

21. The process of claim 1, further comprising:
(iv) converting the compound of formula (I) to a compound of general formula (V):

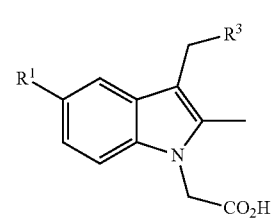

(V)

wherein $R^1$ and $R^3$ are as defined in claim 1;
the process comprising hydrolysing the compound of formula (I).

22. The process of claim 1, further comprising, before (i), a process for the preparation of a compound of formula (II) comprising:

reacting 5-fluoro-2-methyl indole with a compound of the formula (VI):

X—CH$_2$—COOR$^1$     (VI)

where X is a leaving group and R$^1$ is as defined for formula (I).

* * * * *